(12) United States Patent
Wang et al.

(10) Patent No.: US 11,987,627 B2
(45) Date of Patent: May 21, 2024

(54) ANTI-CD47 ANTIBODY AND APPLICATION THEREOF

(71) Applicant: NANJING SANHOME PHARMACEUTICAL CO., LTD., Jiangsu (CN)

(72) Inventors: Yong Wang, Jiangsu (CN); Liwen Zhao, Jiangsu (CN); Qifeng Song, Jiangsu (CN); Yongqiang Zhu, Jiangsu (CN); Yanan Zhang, Jiangsu (CN); Luwei Han, Jiangsu (CN); Liang Jin, Jiangsu (CN); Wenming Wu, Jiangsu (CN)

(73) Assignee: NANJING SANHOME PHARMACEUTICAL CO., LTD., Nanjing (CN)

( * ) Notice: Subject to any disclaimer, the term of this patent is extended or adjusted under 35 U.S.C. 154(b) by 752 days.

(21) Appl. No.: 17/270,947

(22) PCT Filed: Aug. 30, 2019

(86) PCT No.: PCT/CN2019/103673
§ 371 (c)(1),
(2) Date: Feb. 24, 2021

(87) PCT Pub. No.: WO2020/043188
PCT Pub. Date: Mar. 5, 2020

(65) Prior Publication Data
US 2022/0119520 A1    Apr. 21, 2022

(30) Foreign Application Priority Data

Aug. 31, 2018 (CN) .......................... 201811009176.8

(51) Int. Cl.
| | | |
|---|---|---|
| *A61K 39/395* | (2006.01) | |
| *A61P 35/00* | (2006.01) | |
| *C07K 16/28* | (2006.01) | |
| *C07K 16/30* | (2006.01) | |
| *A61K 39/00* | (2006.01) | |

(52) U.S. Cl.
CPC .......... *C07K 16/2803* (2013.01); *A61P 35/00* (2018.01); *A61K 2039/505* (2013.01); *C07K 2317/20* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 2013/0224188 A1* | 8/2013 | Eckelman .......... A61K 39/3955 530/387.9 |
|---|---|---|
| 2017/0081407 A1 | 3/2017 | Grosveld et al. |
| 2018/0250395 A1 | 9/2018 | Pietsch et al. |
| 2019/0023784 A1 | 1/2019 | Chalons-Cottavoz et al. |
| 2020/1405651 | 5/2020 | Wang et al. |

FOREIGN PATENT DOCUMENTS

| CN | 104271757 | 1/2015 |
|---|---|---|
| CN | 15101997 | 11/2015 |
| CN | 105101997 | 11/2015 |
| CN | 107406503 | 11/2017 |
| CN | 107955071 | 4/2018 |
| CN | 108495863 | 9/2018 |
| JP | 2016507555 | 3/2016 |
| JP | 2018502060 | 1/2018 |
| WO | WO 2011/143624 | 11/2011 |
| WO | WO 2014/123580 | 8/2014 |
| WO | WO 2015/191861 | 12/2015 |
| WO | WO 2016/081423 | 5/2016 |
| WO | WO 2017/053423 | 3/2017 |
| WO | WO 2017/121771 | 7/2017 |
| WO | WO 2018/075857 | 4/2018 |

OTHER PUBLICATIONS

Extended European Search Report issued in European Application No. 19853645.0, dated Jun. 3, 2022.
Office Action issued in Chinese Application No. 201910817746.4, Issued Apr. 6, 2022, and English language translation thereof.
Office Action issued in Japanese Application No. 2021-510171, dated May 10, 2022, and English language translation thereof.
Pietsch et al., "Anti-leukemic activity and tolerability of anti-human CD47 monoclonal antibodies." *Blood Cancer J*. Feb. 24, 2017;7(2):e536.
Yu et al., "A novel fully human anti-CD47 antibody as a potential therapy for human neoplasms with good safety." *Biochimie*. Aug. 2018;151:54-66.
English translation of PCT International Search Report issued in International Application No. PCT/CN2019/103673, dated Dec. 5, 2019.

* cited by examiner

*Primary Examiner* — Daniel E Kolker
*Assistant Examiner* — Brianna K Swartwout
(74) *Attorney, Agent, or Firm* — Parker Highlander PLLC

(57) ABSTRACT

The present disclosure relates to the technical field of antibody drugs, and in particular, to an anti-CD47 antibody or an antigen-binding fragment thereof, a pharmaceutical composition comprising the anti-CD47 antibody or the antigen-binding fragment thereof, and applications thereof. The anti-CD47 antibody or the antigen-binding fragment thereof has significant antitumor activity and high affinity with human CD47 protein, can eliminate the capability of SIRPa to bind to CD47 on a surface of a cell, and does not have significant hemoagglutination activity and thus can be applied to the preparation of an anti-tumor drug.

8 Claims, 4 Drawing Sheets

Specification includes a Sequence Listing.

SEQUENCE LISTING

```
<160> NUMBER OF SEQ ID NOS: 74

<210> SEQ ID NO 1
<211> LENGTH: 8
<212> TYPE: PRT
<213> ORGANISM: Artificial
<220> FEATURE:
<223> OTHER INFORMATION: HCDR1

<400> SEQUENCE: 1

Gly Tyr Ile Phe Thr Asp Tyr Tyr
1               5

<210> SEQ ID NO 2
<211> LENGTH: 8
<212> TYPE: PRT
<213> ORGANISM: Artificial
<220> FEATURE:
<223> OTHER INFORMATION: HCDR2

<400> SEQUENCE: 2

Ile Tyr Pro Gly Ser Gly Leu Thr
1               5

<210> SEQ ID NO 3
<211> LENGTH: 12
<212> TYPE: PRT
<213> ORGANISM: Artificial
<220> FEATURE:
<223> OTHER INFORMATION: HCDR3

<400> SEQUENCE: 3

Ala Arg Cys Ser Tyr Gly Ser Ser Phe Pro His Val
1               5                   10

<210> SEQ ID NO 4
<211> LENGTH: 8
<212> TYPE: PRT
<213> ORGANISM: Artificial
<220> FEATURE:
<223> OTHER INFORMATION: HCDR1

<400> SEQUENCE: 4

Gly Tyr Thr Phe Thr Asn Tyr Trp
1               5

<210> SEQ ID NO 5
<211> LENGTH: 8
<212> TYPE: PRT
<213> ORGANISM: Artificial
<220> FEATURE:
<223> OTHER INFORMATION: HCDR2

<400> SEQUENCE: 5

Ile Thr Pro Gly Arg Gly Glu Thr
1               5
```

```
<210> SEQ ID NO 6
<211> LENGTH: 10
<212> TYPE: PRT
<213> ORGANISM: Artificial
<220> FEATURE:
<223> OTHER INFORMATION: HCDR3

<400> SEQUENCE: 6

Ser Arg Trp Gly Leu Arg Arg Gly Asp Tyr
1               5                   10

<210> SEQ ID NO 7
<211> LENGTH: 8
<212> TYPE: PRT
<213> ORGANISM: Artificial
<220> FEATURE:
<223> OTHER INFORMATION: HCDR1

<400> SEQUENCE: 7

Gly Phe Ile Phe Ser Arg Phe Gly
1               5

<210> SEQ ID NO 8
<211> LENGTH: 8
<212> TYPE: PRT
<213> ORGANISM: Artificial
<220> FEATURE:
<223> OTHER INFORMATION: HCDR2

<400> SEQUENCE: 8

Ile Ser Ser Gly Gly Ser Tyr Thr
1               5

<210> SEQ ID NO 9
<211> LENGTH: 14
<212> TYPE: PRT
<213> ORGANISM: Artificial
<220> FEATURE:
<223> OTHER INFORMATION: HCDR3

<400> SEQUENCE: 9

Ala Arg Gln Gly Leu Leu Asp Tyr Leu Tyr Ala Leu Asp Tyr
1               5                   10

<210> SEQ ID NO 10
<211> LENGTH: 8
<212> TYPE: PRT
<213> ORGANISM: Artificial
<220> FEATURE:
<223> OTHER INFORMATION: HCDR1

<400> SEQUENCE: 10

Gly Tyr Thr Phe Thr Asp Tyr Tyr
1               5

<210> SEQ ID NO 11
<211> LENGTH: 12
<212> TYPE: PRT
<213> ORGANISM: Artificial
<220> FEATURE:
<223> OTHER INFORMATION: HCDR3

<400> SEQUENCE: 11

Ala Arg Thr Ser Tyr Gly Ser Ser Phe Pro His Val
1               5                   10
```

```
<210> SEQ ID NO 12
<211> LENGTH: 12
<212> TYPE: PRT
<213> ORGANISM: Artificial
<220> FEATURE:
<223> OTHER INFORMATION: LCDR1

<400> SEQUENCE: 12

Gln Ser Leu Leu Asn Val Asn Asp Gln Lys Asn Tyr
1               5                   10

<210> SEQ ID NO 13
<211> LENGTH: 3
<212> TYPE: PRT
<213> ORGANISM: Artificial
<220> FEATURE:
<223> OTHER INFORMATION: LCDR2

<400> SEQUENCE: 13

Phe Ala Ser
1

<210> SEQ ID NO 14
<211> LENGTH: 9
<212> TYPE: PRT
<213> ORGANISM: Artificial
<220> FEATURE:
<223> OTHER INFORMATION: LCDR3

<400> SEQUENCE: 14

Gln Gln His Tyr Ser Thr Pro Leu Thr
1               5

<210> SEQ ID NO 15
<211> LENGTH: 7
<212> TYPE: PRT
<213> ORGANISM: Artificial
<220> FEATURE:
<223> OTHER INFORMATION: LCDR1

<400> SEQUENCE: 15

Ser Ser Val Ser Ser Ser Tyr
1               5

<210> SEQ ID NO 16
<211> LENGTH: 3
<212> TYPE: PRT
<213> ORGANISM: Artificial
<220> FEATURE:
<223> OTHER INFORMATION: LCDR2

<400> SEQUENCE: 16

Ser Thr Ser
1

<210> SEQ ID NO 17
<211> LENGTH: 9
<212> TYPE: PRT
<213> ORGANISM: Artificial
<220> FEATURE:
<223> OTHER INFORMATION: LCDR3

<400> SEQUENCE: 17

Gln Gln Tyr Ser Gly Tyr Pro Leu Thr
1               5
```

```
<210> SEQ ID NO 18
<211> LENGTH: 6
<212> TYPE: PRT
<213> ORGANISM: Artificial
<220> FEATURE:
<223> OTHER INFORMATION: LCDR1

<400> SEQUENCE: 18

Gln Asp Ile Asn Ser Phe
1               5

<210> SEQ ID NO 19
<211> LENGTH: 3
<212> TYPE: PRT
<213> ORGANISM: Artificial
<220> FEATURE:
<223> OTHER INFORMATION: LCDR2

<400> SEQUENCE: 19

Arg Ala Tyr
1

<210> SEQ ID NO 20
<211> LENGTH: 9
<212> TYPE: PRT
<213> ORGANISM: Artificial
<220> FEATURE:
<223> OTHER INFORMATION: LCDR3

<400> SEQUENCE: 20

Gln Gln Tyr Val Glu Phe Pro Pro Thr
1               5

<210> SEQ ID NO 21
<211> LENGTH: 119
<212> TYPE: PRT
<213> ORGANISM: Artificial
<220> FEATURE:
<223> OTHER INFORMATION: Heavy chain variable region

<400> SEQUENCE: 21

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Ile Phe Thr Asp Tyr
            20                  25                  30

Tyr Met Asn Trp Val Lys Gln Arg Pro Gly Gln Gly Leu Glu Trp Ile
        35                  40                  45

Ala Arg Ile Tyr Pro Gly Ser Gly Leu Thr Tyr Tyr Asn Ala Lys Phe
    50                  55                  60

Lys Gly Lys Ala Thr Val Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Cys Ser Tyr Gly Ser Ser Phe Pro His Val Trp Gly Thr Gly
            100                 105                 110

Thr Thr Val Thr Val Ser Ser
        115

<210> SEQ ID NO 22
<211> LENGTH: 117
<212> TYPE: PRT
<213> ORGANISM: Artificial
<220> FEATURE:
<223> OTHER INFORMATION: Heavy chain variable region
```

```
<400> SEQUENCE: 22

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Glu Lys Phe
    50                  55                  60

Lys Ser Lys Ala Thr Leu Thr Val Asp Thr Ser Ser Thr Ala Tyr
65                  70                  75                  80

Met Gln Leu Thr Ser Leu Thr Ser Glu Asp Ser Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115

<210> SEQ ID NO 23
<211> LENGTH: 121
<212> TYPE: PRT
<213> ORGANISM: Artificial
<220> FEATURE:
<223> OTHER INFORMATION: Heavy chain variable region

<400> SEQUENCE: 23

Glu Val Gln Leu Val Glu Ser Gly Gly Asp Leu Val Glu Pro Gly Gly
1               5                   10                  15

Ser Leu Lys Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Leu Thr Ile Ser Arg Asp Asn Ala Lys Thr Thr Leu Tyr
65                  70                  75                  80

Leu Gln Met Arg Ser Leu Lys Ser Glu Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120

<210> SEQ ID NO 24
<211> LENGTH: 113
<212> TYPE: PRT
<213> ORGANISM: Artificial
<220> FEATURE:
<223> OTHER INFORMATION: Light chain variable region

<400> SEQUENCE: 24

Asp Ile Val Met Thr Gln Ser Pro Phe Ser Leu Ala Met Ser Val Gly
1               5                   10                  15

Gln Lys Val Thr Met Ser Cys Lys Ser Ser Gln Ser Leu Leu Asn Val
            20                  25                  30

Asn Asp Gln Lys Asn Tyr Leu Ala Trp Tyr Gln Gln Lys Pro Gly Gln
        35                  40                  45
```

Ser Pro Lys Leu Leu Val Tyr Phe Ala Ser Thr Arg Glu Ser Gly Val
        50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
                100                 105                 110

Lys

<210> SEQ ID NO 25
<211> LENGTH: 108
<212> TYPE: PRT
<213> ORGANISM: Artificial
<220> FEATURE:
<223> OTHER INFORMATION: Light chain variable region

<400> SEQUENCE: 25

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
                20                  25                  30

Tyr Leu Asn Trp Tyr Gln Gln Lys Ser Gly Ala Ser Pro Lys Leu Trp
            35                  40                  45

Ile Tyr Ser Thr Ser Asn Leu Ala Ser Gly Val Pro Gly Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105

<210> SEQ ID NO 26
<211> LENGTH: 107
<212> TYPE: PRT
<213> ORGANISM: Artificial
<220> FEATURE:
<223> OTHER INFORMATION: Light chain variable region

<400> SEQUENCE: 26

Asp Ile Lys Met Ile Gln Ser Pro Ser Ser Met Tyr Ala Gly Leu Gly
1               5                   10                  15

Glu Arg Val Thr Phe Asn Cys Lys Ala Ser Gln Asp Ile Asn Ser Phe
                20                  25                  30

Leu Cys Trp Phe Gln Gln Lys Pro Gly Lys Ser Pro Arg Pro Leu Ile
            35                  40                  45

Tyr Arg Ala Tyr Arg Leu Val Asp Gly Val Pro Ser Arg Phe Ser Gly
        50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
                85                  90                  95

Thr Phe Gly Ala Gly Thr Met Leu Glu Leu Lys
            100                 105

<210> SEQ ID NO 27

```
<211> LENGTH: 119
<212> TYPE: PRT
<213> ORGANISM: Artificial
<220> FEATURE:
<223> OTHER INFORMATION: Heavy chain variable region

<400> SEQUENCE: 27

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Ile Phe Thr Asp Tyr
            20                  25                  30

Tyr Met Asn Trp Val Lys Gln Arg Pro Gly Gln Gly Leu Glu Trp Ile
        35                  40                  45

Ala Arg Ile Tyr Pro Gly Ser Gly Leu Thr Tyr Tyr Asn Ala Lys Phe
    50                  55                  60

Lys Gly Lys Ala Thr Val Thr Ala Glu Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Thr Ser Tyr Gly Ser Ser Phe Pro His Val Trp Gly Thr Gly
            100                 105                 110

Thr Thr Val Thr Val Ser Ser
        115

<210> SEQ ID NO 28
<211> LENGTH: 107
<212> TYPE: PRT
<213> ORGANISM: Artificial
<220> FEATURE:
<223> OTHER INFORMATION: Light chain variable region

<400> SEQUENCE: 28

Asp Ile Lys Met Ile Gln Ser Pro Ser Ser Met Tyr Ala Gly Leu Gly
1               5                   10                  15

Glu Arg Val Thr Phe Asn Cys Lys Ala Ser Gln Asp Ile Asn Ser Phe
            20                  25                  30

Leu Ala Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
    50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
            85                  90                  95

Thr Phe Gly Ala Gly Thr Met Leu Glu Leu Lys
            100                 105

<210> SEQ ID NO 29
<211> LENGTH: 119
<212> TYPE: PRT
<213> ORGANISM: Artificial
<220> FEATURE:
<223> OTHER INFORMATION: Heavy chain variable region

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Tyr Met Asn Trp Val Arg Gln Ala Pro Gly Gln Gly Leu Glu Trp Ile
            35                  40                  45

Gly Arg Ile Tyr Pro Gly Ser Gly Leu Thr Tyr Tyr Asn Ala Lys Phe
    50                  55                  60

Lys Gly Arg Ala Thr Val Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
            115

<210> SEQ ID NO 30
<211> LENGTH: 117
<212> TYPE: PRT
<213> ORGANISM: Artificial
<220> FEATURE:
<223> OTHER INFORMATION: Heavy chain variable region

<400> SEQUENCE: 30

Gln Val Gln Leu Gln Glu Ser Gly Pro Gly Leu Val Lys Pro Ser Gln
1               5                   10                  15

Thr Leu Ser Leu Thr Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
            35                  40                  45

Gly Asp Ile Thr Pro Gly Arg Gly Glu Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
            115

<210> SEQ ID NO 31
<211> LENGTH: 121
<212> TYPE: PRT
<213> ORGANISM: Artificial
<220> FEATURE:
<223> OTHER INFORMATION: Heavy chain variable region

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
    50                  55                  60

Lys Gly Arg Leu Thr Ile Ser Arg Asp Asn Ala Lys Thr Thr Leu Tyr
65                  70                  75                  80

Leu Gln Met Arg Ser Leu Lys Ser Glu Asp Thr Ala Met Tyr Tyr Cys
                85                  90                  95
```

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120

<210> SEQ ID NO 32
<211> LENGTH: 113
<212> TYPE: PRT
<213> ORGANISM: Artificial
<220> FEATURE:
<223> OTHER INFORMATION: Light chain variable region

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Val
            20                  25                  30

Asn Asp Gln Lys Asn Tyr Leu Ala Trp Tyr Gln Gln Lys Pro Gly Lys
        35                  40                  45

Ala Pro Lys Leu Leu Ile Tyr Phe Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Ser Thr Pro Leu Thr Phe Gly Gln Gly Thr Lys Leu Glu Ile
            100                 105                 110

Lys

<210> SEQ ID NO 33
<211> LENGTH: 108
<212> TYPE: PRT
<213> ORGANISM: Artificial
<220> FEATURE:
<223> OTHER INFORMATION: Light chain variable region

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105

<210> SEQ ID NO 34
<211> LENGTH: 107
<212> TYPE: PRT
<213> ORGANISM: Artificial
<220> FEATURE:
<223> OTHER INFORMATION: Light chain variable region

<400> SEQUENCE: 34

Asp Ile Gln Met Thr Gln Ser Pro Ser Val Ser Ala Ser Ile Gly
1               5                   10                  15

Asp Arg Val Thr Ile Thr Cys Lys Ala Ser Gln Asp Ile Asn Ser Phe
            20                  25                  30

Leu Ala Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
                85                  90                  95

Thr Phe Gly Ala Gly Thr Met Leu Glu Leu Lys
            100                 105

<210> SEQ ID NO 35
<211> LENGTH: 357
<212> TYPE: DNA
<213> ORGANISM: Artificial
<220> FEATURE:
<223> OTHER INFORMATION: Nucleotide sequence encoding heavy chain
      variable region

<400> SEQUENCE: 35
caggtgcagc tggtgcagag cggagccgaa gtgaagaagc ccggtgccag cgtgaaagta      60
agctgcaagg ccagcggcta caccttcacc gactactaca tgaactgggt gaggcaggcc     120
cctggacaag gcctggagtg gatcggcagg atctaccccg cagcggcct gacctactat      180 aacgccaagt tcaagggcag ggccaccgtg accgccgaca gtccaccag caccgtgtac      240 atggagctga gcagcctgag gagcgaggac accgccgtgt attactgcgc caggaccagc     300
tacggcagca gcttccccca cgtgtggggc cagggcacca ccgtgaccgt gagctct        357

<210> SEQ ID NO 36
<211> LENGTH: 351
<212> TYPE: DNA
<213> ORGANISM: Artificial
<220> FEATURE:
<223> OTHER INFORMATION: Nucleotide sequence encoding heavy chain
      variable region

<400> SEQUENCE: 36
caggttcagc tgcaagagag cggtcccggc ctggtgaaac ccagccagac cctgagcctg      60
acctgcaagg ccagcggcta cactttcact aactactgga tcacctgggt gaagcagcga     120
cccggccagg gcctggagtg gatcggcgac atcaccctg ggaggggaga gaccaactac      180
aaccagaagt tcaagggcag ggtgaccctg accgtggaca tcagcgcctc cactgcctat     240
atggagctga gcagcctgag gagcgaggac accgccgtgt actactgcag caggtggggc     300
ctgaggaggg gcgattactg gggccaaggg accagcgtga ccgtgagctc t              351

<210> SEQ ID NO 37
<211> LENGTH: 363
<212> TYPE: DNA
<213> ORGANISM: Artificial
<220> FEATURE:
<223> OTHER INFORMATION: Nucleotide sequence encoding heavy chain
      variable region

<400> SEQUENCE: 37

```
gaggtccagc tgctggagag cggcggtggc ctcgtgcagc ccggaggcag cctgaggctg    60
agctgcgcgg caagcggctt catcttcagc aggttcggca tggcctgggt gaggcagacc   120
ccagacaaga ggctggagtg ggtggcaact atcagcagcg aggaagttta cacctactac   180
cccgacagcg tgaagggcag gctgaccatc agtagggaca cgccaagac cacccctgtac   240 ctgcagatga ggagcctgaa gagcgaggac accgccatgt actactgcgc caggcagggc   300
ctgctcgact atctgtacgc cctggactat tggggccagg gcactgccgt gaccgtgagc   360
agc                                                                 363
```

<210> SEQ ID NO 38
<211> LENGTH: 339
<212> TYPE: DNA
<213> ORGANISM: Artificial
<220> FEATURE:
<223> OTHER INFORMATION: Nucleotide sequence encoding light chain
      variable region

<400> SEQUENCE: 38

```
gacatccaga tgacccagag cccaagcagc ctgagcgcca gcgtgggcga cagggtgacc    60
atcacctgca gagcagcca aagcctgctg aacgtgaacg accagaagaa ctacctggcc   120
tggtatcagc agaagccggg caaggcccc aagctgctca tctactttgc cagcaccagg   180
gagagcggcg tgcccagcag gttcagcggc agcggaagtg gcaccgactt cacccctcacc   240 atcagctccc tgcaacccga ggacttcgcc acctactact gtcaacagca ctacagcaca   300 ccctgacct tcggccaggg caccaagttg gagatcaag                           339
```

<210> SEQ ID NO 39
<211> LENGTH: 324
<212> TYPE: DNA
<213> ORGANISM: Artificial
<220> FEATURE:
<223> OTHER INFORMATION: Nucleotide sequence encoding light chain
      variable region

<400> SEQUENCE: 39

```
gagatcgtgc tgacccagag ccctggcacc ttgagcctga gtcccggaga gagggccacc    60
ctgagctgca gggcctcaag ctccgtgagc agcagctatc tgaattggta tcagcagaag   120
agcggagcca gccccaagct gtggatctac agcaccagca acctggcaag cggcgtgccc   180
ggcaggttca gcggcagtgg cagcgggacc agctacagcc tgaccatcag tagcgtggag   240
gccgaggacg ccgccaccta ctactgccag cagtacagcg ataccctct gaccttcgga   300 gccggaacca agttggaggt gaag                                          324
```

<210> SEQ ID NO 40
<211> LENGTH: 321
<212> TYPE: DNA
<213> ORGANISM: Artificial
<220> FEATURE:
<223> OTHER INFORMATION: Nucleotide sequence encoding light chain
      variable region

<400> SEQUENCE: 40

```
gacatccaga tgacccagag cccaagcagc gtgagcgcca gcatcggcga cagggtgacc    60
ataacctgca aggccagcca agacataaac agcttcctgg catggttcca gcagaagccc   120
ggcaagagcc ccaggcccct gatctacagg gcctacaggc tggtagacgg ggtgcccagc   180
aggttcagcg gcgtgggcag cggccaggac tacagcctga ccatcagcag cctggactac   240
```

```
gaggacctgg gcatctacta ctgccagcag tacgtggagt ccccccgac cttcggtgca    300 gggaccatgc tggagctgaa g                                              321
```

<210> SEQ ID NO 41
<211> LENGTH: 323
<212> TYPE: PRT
<213> ORGANISM: Artificial
<220> FEATURE:
<223> OTHER INFORMATION: CD47 protein

<400> SEQUENCE: 41

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 42

<211> LENGTH: 350
<212> TYPE: PRT
<213> ORGANISM: Artificial
<220> FEATURE:
<223> OTHER INFORMATION: CD47-hFc fusion protein

<400> SEQUENCE: 42

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Glu Pro Lys Ser Cys Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255

Ser Arg Asp Glu Leu Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 43
<211> LENGTH: 124
<212> TYPE: PRT
<213> ORGANISM: Artificial

<220> FEATURE:
<223> OTHER INFORMATION: CD47-his fusion protein

<400> SEQUENCE: 43

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp His His His His His His
        115                 120

<210> SEQ ID NO 44
<211> LENGTH: 354
<212> TYPE: PRT
<213> ORGANISM: Artificial
<220> FEATURE:
<223> OTHER INFORMATION: CD47-mFc fusion protein

<400> SEQUENCE: 44

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Glu Pro Arg Gly Pro Thr Ile
        115                 120                 125

Lys Pro Cys Pro Pro Cys Lys Cys Pro Ala Pro Asn Leu Leu Gly Gly
    130                 135                 140

Pro Ser Val Phe Ile Phe Pro Pro Lys Ile Lys Asp Val Leu Met Ile
145                 150                 155                 160

Ser Leu Ser Pro Ile Val Thr Cys Val Val Asp Val Ser Glu Asp
                165                 170                 175

Asp Pro Asp Val Gln Ile Ser Trp Phe Val Asn Asn Val Glu Val His
            180                 185                 190

Thr Ala Gln Thr Gln Thr His Arg Glu Asp Tyr Asn Ser Thr Leu Arg
        195                 200                 205

Val Val Ser Ala Leu Pro Ile Gln His Gln Asp Trp Met Ser Gly Lys

Glu Phe Lys Cys Lys Val Asn Asn Lys Asp Leu Pro Ala Pro Ile Glu
225                 230                 235                 240

Arg Thr Ile Ser Lys Pro Lys Gly Ser Val Arg Ala Pro Gln Val Tyr
            245                 250                 255

Val Leu Pro Pro Glu Glu Met Thr Lys Lys Gln Val Thr Leu
        260                 265                 270

Thr Cys Met Val Thr Asp Phe Met Pro Glu Asp Ile Tyr Val Glu Trp
        275                 280                 285

Thr Asn Asn Gly Lys Thr Glu Leu Asn Tyr Lys Asn Thr Glu Pro Val
290                 295                 300

Leu Asp Ser Asp Gly Ser Tyr Phe Met Tyr Ser Lys Leu Arg Val Glu
305                 310                 315                 320

Lys Lys Asn Trp Val Glu Arg Asn Ser Tyr Ser Cys Ser Val Val His
                325                 330                 335

Glu Gly Leu His Asn His His Thr Thr Lys Ser Phe Ser Arg Thr Pro
            340                 345                 350

Gly Lys

<210> SEQ ID NO 45
<211> LENGTH: 338
<212> TYPE: PRT
<213> ORGANISM: Artificial
<220> FEATURE:
<223> OTHER INFORMATION: SIRP

<400> SEQUENCE: 45

Glu Leu Gln Val Ile Gln Pro Asp Lys Ser Val Leu Val Ala Ala Gly
1               5                   10                  15

Glu Thr Ala Thr Leu Arg Cys Thr Ala Thr Ser Leu Ile Pro Val Gly
            20                  25                  30

Pro Ile Gln Trp Phe Arg Gly Ala Gly Pro Gly Arg Glu Leu Ile Tyr
        35                  40                  45

Asn Gln Lys Glu Gly His Phe Pro Arg Val Thr Thr Val Ser Asp Leu
50                  55                  60

Thr Lys Arg Asn Asn Met Asp Phe Ser Ile Arg Ile Gly Asn Ile Thr
65                  70                  75                  80

Pro Ala Asp Ala Gly Thr Tyr Tyr Cys Val Lys Phe Arg Lys Gly Ser
                85                  90                  95

Pro Asp Asp Val Glu Phe Lys Ser Gly Ala Gly Thr Glu Leu Ser Val
            100                 105                 110

Arg Ala Lys Pro Ser Ala Pro Val Val Ser Gly Pro Ala Ala Arg Ala
        115                 120                 125

Thr Pro Gln His Thr Val Ser Phe Thr Cys Glu Ser His Gly Phe Ser
    130                 135                 140

Pro Arg Asp Ile Thr Leu Lys Trp Phe Lys Asn Gly Asn Glu Leu Ser
145                 150                 155                 160

Asp Phe Gln Thr Asn Val Asp Pro Val Gly Glu Ser Val Ser Tyr Ser
                165                 170                 175

Ile His Ser Thr Ala Lys Val Val Leu Thr Arg Glu Asp Val His Ser
            180                 185                 190

Gln Val Ile Cys Glu Val Ala His Val Thr Leu Gln Gly Asp Pro Leu
        195                 200                 205

Arg Gly Thr Ala Asn Leu Ser Glu Thr Ile Arg Val Pro Pro Thr Leu
    210                 215                 220

```
Glu Val Thr Gln Gln Pro Val Arg Ala Glu Asn Gln Val Asn Val Thr
225                 230                 235                 240

Cys Gln Val Arg Lys Phe Tyr Pro Gln Arg Leu Gln Leu Thr Trp Leu
            245                 250                 255

Glu Asn Gly Asn Val Ser Arg Thr Glu Thr Ala Ser Thr Val Thr Glu
        260                 265                 270

Asn Lys Asp Gly Thr Tyr Asn Trp Met Ser Trp Leu Leu Val Asn Val
    275                 280                 285

Ser Ala His Arg Asp Asp Val Lys Leu Thr Cys Gln Val Glu His Asp
290                 295                 300

Gly Gln Pro Ala Val Ser Lys Ser His Asp Leu Lys Val Ser Ala His
305                 310                 315                 320

Pro Lys Glu Gln Gly Ser Asn Thr Ala Ala Glu Asn Thr Gly Ser Asn
            325                 330                 335

Glu Arg

<210> SEQ ID NO 46
<211> LENGTH: 466
<212> TYPE: PRT
<213> ORGANISM: Artificial
<220> FEATURE:
<223> OTHER INFORMATION: Heavy chain of AB06.12-4P

<400> SEQUENCE: 46

Met Glu Phe Gly Leu Ser Trp Leu Phe Leu Val Ala Ile Leu Lys Gly
1               5                   10                  15

Val Gln Cys Gln Met Gln Leu Val Gln Ser Gly Ala Glu Val Lys Lys
            20                  25                  30

Thr Gly Ser Ser Val Lys Val Ser Cys Lys Ala Ser Gly Phe Asn Ile
        35                  40                  45

Lys Asp Tyr Tyr Leu His Trp Val Arg Gln Ala Pro Gly Gln Ala Leu
    50                  55                  60

Glu Trp Met Gly Trp Ile Asp Pro Asp Gln Gly Asp Thr Glu Tyr Ala
65                  70                  75                  80

Gln Lys Phe Gln Asp Arg Val Thr Ile Thr Arg Asp Arg Ser Met Ser
                85                  90                  95

Thr Ala Tyr Met Glu Leu Ser Ser Leu Arg Ser Glu Asp Thr Ala Met
            100                 105                 110

Tyr Tyr Cys Asn Ala Ala Tyr Gly Ser Ser Tyr Pro Met Asp Tyr
        115                 120                 125

Trp Gly Gln Gly Thr Thr Val Thr Val Ser Ser Ala Ser Thr Lys Gly
130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240
```

```
Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser Gln Glu
    275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465

<210> SEQ ID NO 47
<211> LENGTH: 236
<212> TYPE: PRT
<213> ORGANISM: Artificial
<220> FEATURE:
<223> OTHER INFORMATION: Light chain of AB06.12-4P

<400> SEQUENCE: 47

Met Asp Met Arg Val Pro Ala Gln Leu Leu Gly Leu Leu Leu Leu Trp
1               5                   10                  15

Phe Pro Gly Ser Arg Cys Asn Ile Gln Met Thr Gln Ser Pro Ser Ala
                20                  25                  30

Met Ser Ala Ser Val Gly Asp Arg Val Thr Ile Thr Cys Lys Ala Ser
            35                  40                  45

Gln Asp Ile His Arg Tyr Leu Ser Trp Phe Gln Gln Lys Pro Gly Lys
        50                  55                  60

Val Pro Lys His Leu Ile Tyr Arg Ala Asn Arg Leu Val Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

Tyr Asp Glu Phe Pro Tyr Thr Phe Gly Gly Gly Thr Lys Val Glu Ile
        115                 120                 125
```

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 48
<211> LENGTH: 117
<212> TYPE: PRT
<213> ORGANISM: Artificial
<220> FEATURE:
<223> OTHER INFORMATION: Humanized heavy chain variable region

<400> SEQUENCE: 48

Gln Val Gln Leu Gln Glu Ser Gly Gly Gly Val Val Gln Pro Gly Arg
1               5                   10                  15

Ser Leu Arg Leu Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Pro Ser Leu
    50                  55                  60

Lys Ser Arg Leu Thr Ile Ser Ile Asp Thr Ser Lys Thr Gln Phe Ser
65                  70                  75                  80

Leu Lys Leu Ser Ser Val Thr Ala Ala Asp Thr Ala Ile Tyr Tyr Cys
                85                  90                  95

Ser Arg Trp Gly Leu Arg Gly Asp Tyr Trp Gly Gln Gly Thr Ser
            100                 105                 110

Val Thr Val Ser Ser
        115

<210> SEQ ID NO 49
<211> LENGTH: 117
<212> TYPE: PRT
<213> ORGANISM: Artificial
<220> FEATURE:
<223> OTHER INFORMATION: Humanized heavy chain variable region

<400> SEQUENCE: 49

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Pro Ser Leu
    50                  55                  60

Lys Ser Arg Leu Thr Ile Ser Ile Asp Thr Ser Lys Thr Gln Phe Ser
65                  70                  75                  80

-continued

Leu Lys Leu Ser Ser Val Thr Ala Ala Asp Thr Ala Ile Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115

<210> SEQ ID NO 50
<211> LENGTH: 117
<212> TYPE: PRT
<213> ORGANISM: Artificial
<220> FEATURE:
<223> OTHER INFORMATION: Humanized heavy chain variable region

<400> SEQUENCE: 50

Gln Val Gln Leu Gln Glu Ser Gly Gly Val Gln Pro Gly Arg
1               5                   10                  15

Ser Leu Arg Leu Ser Cys Lys Ala Ser Gly Tyr Thr Phe Thr Asn Tyr
                20                  25                  30

Trp Ile Thr Trp Val Lys Gln Arg Pro Gly Gln Gly Leu Glu Trp Ile
            35                  40                  45

Gly Asp Ile Thr Pro Gly Arg Gly Glu Thr Asn Tyr Asn Glu Lys Phe
50                  55                  60

Lys Ser Lys Ala Thr Leu Thr Val Asp Thr Ser Ser Thr Ala Tyr
65                  70                  75                  80

Met Gln Leu Thr Ser Leu Thr Ser Glu Asp Ser Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115

<210> SEQ ID NO 51
<211> LENGTH: 118
<212> TYPE: PRT
<213> ORGANISM: Artificial
<220> FEATURE:
<223> OTHER INFORMATION: Humanized heavy chain variable region

<400> SEQUENCE: 51

Gln Val Gln Leu Gln Glu Ser Gly Pro Gly Leu Val Arg Pro Ser Gln
1               5                   10                  15

Thr Leu Ser Leu Thr Cys Lys Ala Ser Gly Tyr Thr Phe Thr Asn Tyr
                20                  25                  30

Trp Ile Thr Trp Val Lys Gln Arg Pro Gly Gln Gly Leu Glu Trp Ile
            35                  40                  45

Gly Asp Ile Thr Pro Gly Arg Gly Glu Thr Asn Tyr Asn Pro Ser Leu
50                  55                  60

Lys Ser Arg Leu Thr Ile Ser Ile Asp Thr Ser Lys Thr Gln Phe Ser
65                  70                  75                  80

Leu Lys Leu Ser Ser Val Thr Ala Ala Asp Thr Ala Ile Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser His
        115

-continued

```
<210> SEQ ID NO 52
<211> LENGTH: 117
<212> TYPE: PRT
<213> ORGANISM: Artificial
<220> FEATURE:
<223> OTHER INFORMATION: Humanized heavy chain variable region

<400> SEQUENCE: 52

Gln Val Gln Leu Gln Glu Ser Gly Pro Gly Leu Val Lys Pro Ser Gln
1               5                   10                  15

Thr Leu Ser Leu Thr Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115

<210> SEQ ID NO 53
<211> LENGTH: 117
<212> TYPE: PRT
<213> ORGANISM: Artificial
<220> FEATURE:
<223> OTHER INFORMATION: Humanized heavy chain variable region

<400> SEQUENCE: 53

Gln Val Gln Leu Gln Glu Ser Gly Gly Gly Val Val Gln Pro Gly Arg
1               5                   10                  15

Ser Leu Arg Leu Ser Cys Lys Ala Ser Gly Tyr Thr Phe Thr Asn Tyr
            20                  25                  30

Trp Ile Thr Trp Val Lys Gln Arg Pro Gly Gln Gly Leu Glu Trp Ile
        35                  40                  45

Gly Asp Ile Thr Pro Gly Arg Gly Glu Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Leu Arg Arg Gly Asp Tyr Trp Gly Gln Gly Thr Ser
            100                 105                 110

Val Thr Val Ser Ser
        115

<210> SEQ ID NO 54
<211> LENGTH: 108
<212> TYPE: PRT
<213> ORGANISM: Artificial
<220> FEATURE:
<223> OTHER INFORMATION: Humanized light chain variable region

<400> SEQUENCE: 54

Glu Ile Val Leu Thr Gln Ser Pro Ala Thr Leu Ser Leu Ser Pro Gly
1               5                   10                  15
```

Glu Arg Ala Thr Leu Ser Cys Arg Ala Ser Ser Val Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105

<210> SEQ ID NO 55
<211> LENGTH: 108
<212> TYPE: PRT
<213> ORGANISM: Artificial
<220> FEATURE:
<223> OTHER INFORMATION: Humanized light chain variable region

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Ser Arg Phe Ser
50                  55                  60

Gly Ser Gly Ser Gly Thr Ser Phe Thr Leu Thr Ile Ser Ser Leu Gln
65                  70                  75                  80

Pro Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105

<210> SEQ ID NO 56
<211> LENGTH: 108
<212> TYPE: PRT
<213> ORGANISM: Artificial
<220> FEATURE:
<223> OTHER INFORMATION: Humanized light chain variable region

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys

-continued

```
<210> SEQ ID NO 57
<211> LENGTH: 108
<212> TYPE: PRT
<213> ORGANISM: Artificial
<220> FEATURE:
<223> OTHER INFORMATION: Humanized light chain variable region

<400> SEQUENCE: 57

Glu Ile Val Met Thr Gln Ser Pro Ala Thr Leu Ser Leu Ser Pro Gly
1               5                   10                  15

Glu Arg Ala Thr Leu Ser Cys Arg Ala Ser Ser Val Ser Ser Ser
            20                  25                  30

Tyr Leu Asn Trp Tyr Gln Gln Lys Ser Gly Ala Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Val Lys
            100                 105

<210> SEQ ID NO 58
<211> LENGTH: 121
<212> TYPE: PRT
<213> ORGANISM: Artificial
<220> FEATURE:
<223> OTHER INFORMATION: Humanized heavy chain variable region

<400> SEQUENCE: 58

Glu Val Gln Leu Val Glu Ser Gly Gly Asp Leu Val Glu Pro Gly Gly
1               5                   10                  15

Ser Leu Lys Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
        35                  40                  45

Ala Thr Ile Ser Ser Gly Gly Ser Tyr Thr Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120

<210> SEQ ID NO 59
<211> LENGTH: 121
<212> TYPE: PRT
<213> ORGANISM: Artificial
<220> FEATURE:
<223> OTHER INFORMATION: Humanized heavy chain variable region

<400> SEQUENCE: 59

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Leu Thr Ile Ser Arg Asp Asn Ala Lys Thr Thr Leu Tyr
 65                  70                  75                  80

Leu Gln Met Arg Ser Leu Lys Ser Glu Asp Thr Ala Met Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120
```

<210> SEQ ID NO 60
<211> LENGTH: 121
<212> TYPE: PRT
<213> ORGANISM: Artificial
<220> FEATURE:
<223> OTHER INFORMATION: Humanized heavy chain variable region

<400> SEQUENCE: 60

```
Leu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
            35                  40                  45

Ala Thr Ile Ser Ser Gly Gly Ser Tyr Thr Asn Tyr Asn Gln Lys Phe
        50                  55                  60

Lys Gly Arg Val Thr Leu Thr Val Asp Ile Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gln Gly Leu Leu Asp Tyr Leu Tyr Ala Leu Asp Tyr Trp Gly
            100                 105                 110

Gln Gly Thr Ala Val Thr Val Ser Ser
        115                 120
```

<210> SEQ ID NO 61
<211> LENGTH: 121
<212> TYPE: PRT
<213> ORGANISM: Artificial
<220> FEATURE:
<223> OTHER INFORMATION: Humanized heavy chain variable region

<400> SEQUENCE: 61

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ile Phe Ser Arg Phe
            20                  25                  30

Gly Met Ala Trp Val Arg Gln Thr Pro Asp Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Leu Thr Ile Ser Arg Asp Asn Ala Lys Thr Thr Leu Tyr
```

```
                65                  70                  75                  80
Leu Gln Met Arg Ser Leu Lys Ser Glu Asp Thr Ala Met Tyr Tyr Cys
                    85                  90                  95

Ala Arg Gln Gly Leu Leu Asp Tyr Leu Tyr Ala Leu Asp Tyr Trp Gly
                100                 105                 110

Gln Gly Thr Ala Val Thr Val Ser Ser
                115                 120

<210> SEQ ID NO 62
<211> LENGTH: 121
<212> TYPE: PRT
<213> ORGANISM: Artificial
<220> FEATURE:
<223> OTHER INFORMATION: Humanized heavy chain variable region

<400> SEQUENCE: 62

Leu Val Gln Leu Val Glu Ser Gly Gly Gly Leu Ile Gln Pro Gly Gly
1               5                   10                  15

Ser Leu Arg Leu Ser Cys Ala Ala Ser Gly Phe Ile Phe Ser Arg Phe
                20                  25                  30

Gly Met Ala Trp Val Arg Gln Thr Pro Asp Lys Arg Leu Glu Trp Val
                35                  40                  45

Ala Thr Ile Ser Ser Gly Gly Ser Tyr Thr Arg Tyr Ser Pro Ser Phe
            50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                    85                  90                  95

Ala Arg Gln Gly Leu Leu Asp Tyr Leu Tyr Ala Leu Asp Tyr Trp Gly
                100                 105                 110

Gln Gly Thr Ala Val Thr Val Ser Ser
                115                 120

<210> SEQ ID NO 63
<211> LENGTH: 121
<212> TYPE: PRT
<213> ORGANISM: Artificial
<220> FEATURE:
<223> OTHER INFORMATION: Humanized heavy chain variable region

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
                20                  25                  30

Gly Met Ala Trp Val Arg Gln Thr Pro Asp Lys Arg Leu Glu Trp Val
                35                  40                  45

Ala Thr Ile Ser Ser Gly Gly Ser Tyr Thr Arg Tyr Ser Pro Ser Phe
            50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                    85                  90                  95

Ala Arg Gln Gly Leu Leu Asp Tyr Leu Tyr Ala Leu Asp Tyr Trp Gly
                100                 105                 110

Gln Gly Thr Ala Val Thr Val Ser Ser
                115                 120
```

```
<210> SEQ ID NO 64
<211> LENGTH: 107
<212> TYPE: PRT
<213> ORGANISM: Artificial
<220> FEATURE:
<223> OTHER INFORMATION: Humanized light chain variable region

<400> SEQUENCE: 64

Asp Ile Gln Met Thr Gln Ser Pro Ser Ser Val Ser Ala Ser Ile Gly
1               5                   10                  15

Asp Arg Val Thr Ile Thr Cys Lys Ala Ser Gln Asp Ile Asn Ser Phe
            20                  25                  30

Leu Thr Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
50                  55                  60

Val Gly Ser Gly Gln Asp Tyr Ser Leu Thr Ile Ser Ser Leu Asp Tyr
65                  70                  75                  80

Glu Asp Leu Gly Ile Tyr Tyr Cys Gln Gln Tyr Val Glu Phe Pro Pro
                85                  90                  95

Thr Phe Gly Ala Gly Thr Met Leu Glu Leu Lys
            100                 105

<210> SEQ ID NO 65
<211> LENGTH: 107
<212> TYPE: PRT
<213> ORGANISM: Artificial
<220> FEATURE:
<223> OTHER INFORMATION: Humanized light chain variable region

<400> SEQUENCE: 65

Asp Ile Gln Met Thr Gln Ser Pro Ser Ser Val Ser Ala Ser Ile Gly
1               5                   10                  15

Asp Arg Val Thr Ile Thr Cys Lys Ala Ser Gln Asp Ile Asn Ser Phe
            20                  25                  30

Leu Thr Trp Phe Gln Gln Lys Pro Gly Lys Ser Pro Arg Pro Leu Ile
        35                  40                  45

Tyr Arg Ala Tyr Arg Leu Val Asp Gly Val Pro Ser Arg Phe Ser Gly
50                  55                  60

Ser Gly Ser Gly Thr Tyr Phe Thr Leu Thr Ile Ser Ser Leu Gln Ala
65                  70                  75                  80

Glu Asp Phe Ala Val Tyr Tyr Cys Gln Gln Tyr Val Glu Phe Pro Pro
                85                  90                  95

Thr Phe Gly Ala Gly Thr Met Leu Glu Leu Lys
            100                 105

<210> SEQ ID NO 66
<211> LENGTH: 107
<212> TYPE: PRT
<213> ORGANISM: Artificial
<220> FEATURE:
<223> OTHER INFORMATION: Humanized light chain variable region

<400> SEQUENCE: 66

Asp Ile Lys Met Ile Gln Ser Pro Ser Ser Met Tyr Ala Gly Leu Gly
1               5                   10                  15

Glu Arg Val Thr Phe Asn Cys Lys Ala Ser Gln Asp Ile Asn Ser Phe
            20                  25                  30

Leu Thr Trp Phe Gln Gln Lys Pro Gly Lys Ser Pro Arg Pro Leu Ile
```

35                  40                  45
Tyr Arg Ala Tyr Arg Leu Val Asp Gly Val Pro Ser Arg Phe Ser Gly
        50                  55                  60
Ser Gly Ser Gly Thr Tyr Phe Thr Leu Thr Ile Ser Ser Leu Gln Ala
65                  70                  75                  80
Glu Asp Phe Ala Val Tyr Tyr Cys Gln Gln Tyr Val Glu Phe Pro Pro
                85                  90                  95
Thr Phe Gly Ala Gly Thr Met Leu Glu Leu Lys
            100                 105

<210> SEQ ID NO 67
<211> LENGTH: 107
<212> TYPE: PRT
<213> ORGANISM: Artificial
<220> FEATURE:
<223> OTHER INFORMATION: Humanized light chain variable region

<400> SEQUENCE: 67

Asp Ile Gln Met Thr Gln Ser Pro Ser Ser Val Ser Ala Ser Ile Gly
1               5                   10                  15
Asp Arg Val Thr Ile Thr Cys Lys Ala Ser Gln Asp Ile Asn Ser Phe
            20                  25                  30
Leu Thr Trp Phe Gln Gln Lys Pro Gly Lys Ser Pro Arg Pro Leu Ile
        35                  40                  45
Tyr Arg Ala Tyr Arg Leu Val Asp Gly Val Pro Asp Arg Phe Ser Gly
    50                  55                  60
Ser Gly Ser Gly Thr Asp Phe Thr Leu Thr Ile Ser Ser Leu Gln Ala
65                  70                  75                  80
Glu Asp Val Ala Val Tyr Tyr Cys Gln Gln Tyr Val Glu Phe Pro Pro
                85                  90                  95
Thr Phe Gly Ala Gly Thr Met Leu Glu Leu Lys
            100                 105

<210> SEQ ID NO 68
<211> LENGTH: 107
<212> TYPE: PRT
<213> ORGANISM: Artificial
<220> FEATURE:
<223> OTHER INFORMATION: Humanized light chain variable region

<400> SEQUENCE: 68

Asp Ile Lys Met Ile Gln Ser Pro Ser Ser Met Tyr Ala Gly Leu Gly
1               5                   10                  15
Glu Arg Val Thr Phe Asn Cys Lys Ala Ser Gln Asp Ile Asn Ser Phe
            20                  25                  30
Leu Thr Trp Phe Gln Gln Lys Pro Gly Lys Ser Pro Arg Pro Leu Ile
        35                  40                  45
Tyr Arg Ala Tyr Arg Leu Val Asp Gly Val Pro Ser Arg Phe Ser Gly
    50                  55                  60
Val Gly Ser Gly Gln Asp Tyr Ser Leu Thr Ile Ser Ser Leu Asp Tyr
65                  70                  75                  80
Glu Asp Leu Gly Ile Tyr Tyr Cys Gln Gln Tyr Val Glu Phe Pro Pro
                85                  90                  95
Thr Phe Gly Ala Gly Thr Met Leu Glu Leu Lys
            100                 105

<210> SEQ ID NO 69
<211> LENGTH: 119

```
<212> TYPE: PRT
<213> ORGANISM: Artificial
<220> FEATURE:
<223> OTHER INFORMATION: Humanized heavy chain variable region

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Arg Ile Tyr Pro Gly Ser Gly Leu Thr Tyr Tyr Asn Ala Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115

<210> SEQ ID NO 70
<211> LENGTH: 119
<212> TYPE: PRT
<213> ORGANISM: Artificial
<220> FEATURE:
<223> OTHER INFORMATION: Humanized heavy chain variable region

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Arg Ile Tyr Pro Gly Ser Gly Leu Thr Tyr Tyr Asn Ala Lys Phe
    50                  55                  60

Lys Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
        115

<210> SEQ ID NO 71
<211> LENGTH: 119
<212> TYPE: PRT
<213> ORGANISM: Artificial
<220> FEATURE:
<223> OTHER INFORMATION: Humanized heavy chain variable region

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
            20                  25                  30
Tyr Met Asn Trp Val Arg Gln Ala Pro Gly Gln Gly Leu Glu Trp Ile
        35                  40                  45

Gly Arg Ile Tyr Pro Gly Ser Gly Leu Thr Tyr Tyr Asn Ala Lys Phe
50                  55                  60

Lys Gly Arg Ala Thr Val Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Ser Tyr Gly Ser Ser Phe Pro His Val Trp Gly Gln Gly
            100                 105                 110

Thr Thr Val Thr Val Ser Ser
            115

<210> SEQ ID NO 72
<211> LENGTH: 119
<212> TYPE: PRT
<213> ORGANISM: Artificial
<220> FEATURE:
<223> OTHER INFORMATION: Humanized heavy chain variable region

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Arg Ile Tyr Pro Gly Ser Gly Leu Thr Tyr Tyr Asn Ala Lys Phe
50                  55                  60

Lys Gly Arg Ala Thr Val Thr Ala Asp Lys Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Thr Ser Tyr Gly Ser Ser Phe Pro His Val Trp Gly Gln Gly
            100                 105                 110

Thr Thr Val Thr Val Ser Ser
            115

<210> SEQ ID NO 73
<211> LENGTH: 113
<212> TYPE: PRT
<213> ORGANISM: Artificial
<220> FEATURE:
<223> OTHER INFORMATION: Humanized light chain variable region

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Val
            20                  25                  30

Asn Asp Gln Lys Asn Tyr Leu Ala Trp Tyr Gln Gln Lys Pro Gly Lys
        35                  40                  45

Ala Pro Lys Leu Leu Ile Tyr Phe Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80
```

```
Ile Ser Ser Leu Gln Pro Glu Asp Phe Ala Thr Tyr Tyr Cys Gln Gln
                85                  90                  95

His Tyr Ser Thr Pro Leu Thr Phe Gly Gln Gly Thr Lys Leu Glu Ile
            100                 105                 110

Lys

<210> SEQ ID NO 74
<211> LENGTH: 113
<212> TYPE: PRT
<213> ORGANISM: Artificial
<220> FEATURE:
<223> OTHER INFORMATION: Humanized light chain variable region

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Val
            20                  25                  30

Asn Asp Gln Lys Asn Tyr Leu Ala Trp Tyr Gln Lys Pro Gly Lys
        35                  40                  45

Ala Pro Lys Leu Leu Val Tyr Phe Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

His Tyr Ser Thr Pro Leu Thr Phe Gly Gln Gly Thr Lys Leu Glu Ile
            100                 105                 110

Lys
```

ANTI-CD47 ANTIBODY AND APPLICATION THEREOF

CROSS REFERENCE TO RELATED APPLICATIONS

This application is a national phase application under 35 U.S.C. § 371 of International Application No. PCT/CN2019/103673, filed Aug. 30, 2019, which claims the benefit of priority of Chinese Patent Application No. 201811009176.8, filed on Aug. 31, 2018, the disclosures of each of which are hereby incorporated by reference.

Pursuant to 37 C.F.R. 1.821(c), a sequence listing is submitted herewith as an ASCII compliant text file named "UNITP0052US_ST25.txt", created on Feb. 19, 2021 and having a size of ~71 kilobytes. The content of the aforementioned file is hereby incorporated by reference in its entirety.

FIELD

The present disclosure relates to the technical field of antibody drugs, and in particular, to an anti-CD47 antibody or an antigen-binding fragment thereof, a pharmaceutical composition comprising the anti-CD47 antibody or the antigen-binding fragment thereof, and uses thereof.

BACKGROUND

CD47 protein, also known as integrin-associated protein (IAP), is a five-span transmembrane glycoprotein belonging to the IgG superfamily and widely expressed in different tissues and cells. CD47 can bind to the ligand TSP-1 or SIRPα to regulate different cellular functions, including migration, adhesion and apoptosis of cells, axon extension, cytokine production as well as T cell activation. SIRPα is a transmembrane protein containing a typical immunoreceptor tyrosine-based inhibitory motif (ITIM), and mainly expressed on the surface of the cell membrane of myeloid hematopoietic cells, such as macrophages, dendritic cells, etc. The binding of CD47 to SIRPα leads to phosphorylation of ITIMs and consequent recruitment of SHP-1/SHP-2, which further inhibit the accumulation of myosin IIA in phagocytic synapses, and ultimately inhibit the phagocytic function of phagocytes.

The "immune escape" of tumor cells is considered as the main mechanism of tumorigenesis, tumor development and drug resistance. Through high expression of CD47 molecules, which interact with SIRPα on the surface of macrophages, tumor cells can significantly inhibit the phagocytic activity of macrophages and avoid being swallowed by macrophages. When the binding of CD47 to SIRPα is blocked, the immune suppression or immune tolerance caused by tumor can be eliminated, and tumor cells can be effectively killed. This provides a very powerful theoretical basis for targeting CD47 as a target of targeted tumor immunotherapy.

In recent years, numerous studies have been conducted on various treatments targeting CD47/SIRPα signaling pathway at home and abroad, such as anti-CD47 antibody, anti-SIRPα antibody, recombinant SIRPα protein, and bispecific antibody. Among them, CD47 blocking antibody is believed to be the most promising tumor treatment regimen. The effectiveness of human CD47 blocking monoclonal antibody has been confirmed in diverse preclinical models, such as lymphoma, bladder cancer, colon cancer, glioblastoma, breast cancer, acute lymphoblastic leukemia, acute myeloid leukemia, and the like.

Furthermore, since red blood cells and platelets also express CD47 molecules, when the antibody blocks the interaction between CD47 and SIRPα, it is likely that these cells may lose the protection of "don't eat me" signal and thereby be subjected to phagocytosis by macrophages. Therefore, the side effects of anti-CD47 antibody should be avoided, such as degradation of platelets, agglutination of red blood cells, depletion of red blood cells, and anemia, etc. These are also important considerations when applying anti-CD47 antibody.

Therefore, there is a need for providing an anti-CD47 antibody or antigen-binding fragment thereof, which has excellent antitumor activity and does not have significant hemagglutination activity.

SUMMARY

One aspect of the present disclosure provides an anti-CD47 antibody or antigen-binding fragment thereof, comprising a heavy chain variable region and/or a light chain variable region, wherein the heavy chain variable region comprises complementarity determining region 1 of the heavy chain variable region (HCDR1), complementarity determining region 2 of the heavy chain variable region (HCDR2), and/or complementarity determining region 3 of the heavy chain variable region (HCDR3); and the light chain variable region comprises complementarity determining region 1 of the light chain variable region (LCDR1), complementarity determining region 2 of the light chain variable region (LCDR2), and/or complementarity determining region 3 of the light chain variable region (LCDR3).

In some embodiments, the present disclosure provides an anti-CD47 antibody or antigen-binding fragment thereof, comprising a heavy chain variable region and a light chain variable region, wherein
  (1) the heavy chain variable region comprises HCDR1, HCDR2 and HCDR3, selected from the group consisting of:
    (a1) amino acid sequences as set forth in SEQ ID NOs: 1, 2 and 3,
    (a2) amino acid sequences as set forth in SEQ ID NOs: 10, 2 and 11,
    (a3) amino acid sequences as set forth in SEQ ID NOs: 4, 5 and 6,
    (a4) amino acid sequences as set forth in SEQ ID NOs: 7, 8 and 9, and
    (a5) CDRs having at least 85% sequence identity to the amino acid sequences set forth in (a1), (a2), (a3), or (a4); and
  (2) the light chain variable region comprises LCDR1, LCDR2 and LCDR3, selected from the group consisting of:
    (a6) amino acid sequences as set forth in SEQ ID NOs: 12, 13 and 14,
    (a7) amino acid sequences as set forth in SEQ ID NOs: 15, 16 and 17,
    (a8) amino acid sequences as set forth in SEQ ID NOs: 18, 19 and 20, and
    (a9) CDRs having at least 85% sequence identity to the amino acid sequences set forth in (a6), (a7), or (a8).

In a specific embodiment, the present disclosure provides an anti-CD47 antibody or antigen-binding fragment thereof, comprising a heavy chain variable region and a light chain variable region, wherein the heavy chain variable region comprises HCDR1, HCDR2, and HCDR3 set forth in SEQ ID NOs: 1, 2 and 3 respectively, or the CDRs having at least 85% sequence identity to the amino acid sequences set forth in SEQ ID NOs: 1, 2 and 3; and the light chain variable region comprises LCDR1, LCDR2 and LCDR3 set forth in SEQ ID NOs: 12, 13 and 14 respectively, or the CDRs having at least 85% sequence identity to the amino acid sequences set forth in SEQ ID NOs: 12, 13 and 14.

In a specific embodiment, the present disclosure provides an anti-CD47 antibody or antigen-binding fragment thereof, comprising a heavy chain variable region and a light chain variable region, wherein the heavy chain variable region comprises HCDR1, HCDR2, and HCDR3 set forth in SEQ ID NOs: 10, 2 and 11 respectively, or the CDRs having at least 85% sequence identity to the amino acid sequences set forth in SEQ ID NOs: 10, 2 and 11; and the light chain variable region comprises LCDR1, LCDR2 and LCDR3 set forth in SEQ ID NOs: 12, 13 and 14 respectively, or the CDRs having at least 85% sequence identity to the amino acid sequences set forth in SEQ ID NOs: 12, 13 and 14.

In a specific embodiment, the present disclosure provides an anti-CD47 antibody or antigen-binding fragment thereof, comprising a heavy chain variable region and a light chain variable region, wherein the heavy chain variable region comprises HCDR1, HCDR2, and HCDR3 set forth in SEQ ID NOs: 4, 5 and 6 respectively, or the CDRs having at least 85% sequence identity to the amino acid sequences set forth in SEQ ID NOs: 4, 5 and 6; and the light chain variable region comprises LCDR1, LCDR2 and LCDR3 set forth in SEQ ID NOs: 15, 16 and 17 respectively, or the CDRs having at least 85% sequence identity to the amino acid sequences set forth in SEQ ID NOs: 15, 16 and 17.

In a specific embodiment, the present disclosure provides an anti-CD47 antibody or antigen-binding fragment thereof, comprising a heavy chain variable region and a light chain variable region, wherein the heavy chain variable region comprises HCDR1, HCDR2, and HCDR3 set forth in SEQ ID NOs: 7, 8 and 9 respectively, or the CDRs having at least 85% sequence identity to the amino acid sequences set forth in SEQ ID NOs: 7, 8 and 9; and the light chain variable region comprises LCDR1, LCDR2 and LCDR3 set forth in SEQ ID NOs: 18, 19 and 20 respectively, or the CDRs having at least 85% sequence identity to the amino acid sequences set forth in SEQ ID NOs: 18, 19 and 20.

In some specific embodiments, the anti-CD47 antibody or antigen-binding fragment thereof according to the present disclosure is a monoclonal antibody or antigen-binding fragment thereof.

In some specific embodiments, the anti-CD47 antibody or antigen-binding fragment thereof according to the present disclosure is a murine-derived antibody or antigen-binding fragment thereof, a chimeric antibody or antigen-binding fragment thereof, or a humanized antibody or antigen-binding fragment thereof.

In some specific embodiments, the present disclosure provides an anti-CD47 antibody or antigen-binding fragment thereof, comprising a heavy chain variable region and a light chain variable region, wherein
(1) the amino acid sequence of the heavy chain variable region is selected from:
(b1) amino acid sequences as set forth in SEQ ID NO: 21, SEQ ID NO: 22, SEQ ID NO: 23, and SEQ ID NO: 27,
(b2) amino acid sequences derived from the amino acid sequences set forth in (b1) by substitution, deletion or addition of one or more amino acids and functionally identical or similar to the amino acid sequences set forth in (b1), and
(b3) amino acid sequences having at least 80% sequence identity to the amino acid sequences set forth in (b1); and
(2) the amino acid sequence of the light chain variable region is selected from:
(b4) amino acid sequences as set forth in SEQ ID NO: 24, SEQ ID NO: 25, SEQ ID NO: 26, and SEQ ID NO: 28,
(b5) amino acid sequences derived from the amino acid sequences set forth in (b4) by substitution, deletion or addition of one or more amino acids and functionally identical or similar to the amino acid sequences set forth in (b4), and
(b6) amino acid sequences having at least 80% sequence identity to the amino acid sequences set forth in (b4).

In some specific embodiments, the present disclosure provides an anti-CD47 antibody or antigen-binding fragment thereof, wherein the amino acid sequence of the heavy chain variable region is selected from the group consisting of SEQ ID NO: 21, the amino acid sequence derived from SEQ ID NO: 21 by substitution, deletion or addition of one or more amino acids and functionally identical to SEQ ID NO: 21, and the amino acid sequence having at least 85% sequence identity to SEQ ID NO: 21; and the amino acid sequence of the light chain variable region is selected from the group consisting of SEQ ID NO: 24, the amino acid sequence derived from SEQ ID NO: 24 by substitution, deletion or addition of one or more amino acids and functionally identical to SEQ ID NO: 24, and the amino acid sequence having at least 85% sequence identity to SEQ ID NO: 24.

In some specific embodiments, the present disclosure provides an anti-CD47 antibody or antigen-binding fragment thereof, wherein the amino acid sequence of the heavy chain variable region is selected from the group consisting of SEQ ID NO: 22, the amino acid sequence derived from SEQ ID NO: 22 by substitution, deletion or addition of one or more amino acids and functionally identical to SEQ ID NO: 22, and the amino acid sequence having at least 85% sequence identity to SEQ ID NO: 22; and the amino acid sequence of the light chain variable region is selected from the group consisting of SEQ ID NO: 25, the amino acid sequence derived from SEQ ID NO: 25 by substitution, deletion or addition of one or more amino acids and functionally identical to SEQ ID NO: 25, and the amino acid sequence having at least 85% sequence identity to SEQ ID NO: 25.

In some specific embodiments, the present disclosure provides an anti-CD47 antibody or antigen-binding fragment thereof, wherein the amino acid sequence of the heavy chain variable region is selected from the group consisting of SEQ ID NO: 23, the amino acid sequence derived from SEQ ID NO: 23 by substitution, deletion or addition of one or more amino acids and functionally identical to SEQ ID NO: 23, and the amino acid sequence having at least 85% sequence identity to SEQ ID NO: 23; and the amino acid sequence of the light chain variable region is selected from the group consisting of SEQ ID NO: 26, the amino acid sequence derived from SEQ ID NO: 26 by substitution, deletion or addition of one or more amino acids and functionally identical to SEQ ID NO: 26, and the amino acid sequence having at least 85% sequence identity to SEQ ID NO: 26.

In some specific embodiments, the present disclosure provides an anti-CD47 antibody or antigen-binding fragment thereof, wherein the amino acid sequence of the heavy chain variable region is selected from the group consisting of SEQ ID NO: 27, the amino acid sequence derived from SEQ ID NO: 27 by substitution, deletion or addition of one or more amino acids and functionally identical to SEQ ID NO: 27, and the amino acid sequence having at least 85% sequence identity to SEQ ID NO: 27; and the amino acid sequence of the light chain variable region is selected from the group consisting of SEQ ID NO: 24, the amino acid sequence derived from SEQ ID NO: 24 by substitution, deletion or addition of one or more amino acids and functionally identical to SEQ ID NO: 24, and the amino acid sequence having at least 85% sequence identity to SEQ ID NO: 24.

In some specific embodiments, the present disclosure provides an anti-CD47 antibody or antigen-binding fragment thereof, wherein the amino acid sequence of the heavy chain variable region is selected from the group consisting of SEQ ID NO: 23, the amino acid sequence derived from SEQ ID NO: 23 by substitution, deletion or addition of one or more amino acids and functionally identical to SEQ ID NO: 23, and the amino acid sequence having at least 85% sequence identity to SEQ ID NO: 23; and the amino acid sequence of the light chain variable region is selected from the group consisting of SEQ ID NO: 28, the amino acid sequence derived from SEQ ID NO: 28 by substitution, deletion or addition of one or more amino acids and functionally identical to SEQ ID NO: 28, and the amino acid sequence having at least 85% sequence identity to SEQ ID NO: 28.

In some specific embodiments, the present disclosure provides an anti-CD47 antibody or antigen-binding fragment thereof, wherein the amino acid sequence of the heavy chain variable region is selected from the group consisting of SEQ ID NO: 21, the amino acid sequence derived from SEQ ID NO: 21 by substitution, deletion or addition of one or more amino acids and functionally identical to SEQ ID NO: 21, and the amino acid sequence having at least 85% sequence identity to SEQ ID NO: 21, and comprises HCDR1, HCDR2, and HCDR3 set forth in SEQ ID NOs: 1, 2 and 3; and the amino acid sequence of the light chain variable region is selected from the group consisting of SEQ ID NO: 24, the amino acid sequence derived from SEQ ID NO: 24 by substitution, deletion or addition of one or more amino acids and functionally identical to SEQ ID NO: 24, and the amino acid sequence having at least 85% sequence identity to SEQ ID NO: 24, and comprises LCDR1, LCDR2 and LCDR3 set forth in SEQ ID NOs: 12, 13 and 14.

In some specific embodiments, the present disclosure provides an anti-CD47 antibody or antigen-binding fragment thereof, wherein the amino acid sequence of the heavy chain variable region is selected from the group consisting of SEQ ID NO: 22, the amino acid sequence derived from SEQ ID NO: 22 by substitution, deletion or addition of one or more amino acids and functionally identical to SEQ ID NO: 22, and the amino acid sequence having at least 85% sequence identity to SEQ ID NO: 22, and comprises HCDR1, HCDR2, and HCDR3 set forth in SEQ ID NOs: 4, 5 and 6; and the amino acid sequence of the light chain variable region is selected from the group consisting of SEQ ID NO: 25, the amino acid sequence derived from SEQ ID NO: 25 by substitution, deletion or addition of one or more amino acids and functionally identical to SEQ ID NO: 25, and the amino acid sequence having at least 85% sequence identity to SEQ ID NO: 25, and comprises LCDR1, LCDR2 and LCDR3 set forth in SEQ ID NOs: 15, 16 and 17.

In some specific embodiments, the present disclosure provides an anti-CD47 antibody or antigen-binding fragment thereof, wherein the amino acid sequence of the heavy chain variable region is selected from the group consisting of SEQ ID NO: 23, the amino acid sequence derived from SEQ ID NO: 23 by substitution, deletion or addition of one or more amino acids and functionally identical to SEQ ID NO: 23, and the amino acid sequence having at least 85% sequence identity to SEQ ID NO: 23, and comprises HCDR1, HCDR2, and HCDR3 set forth in SEQ ID NOs: 7, 8 and 9; and the amino acid sequence of the light chain variable region is selected from the group consisting of SEQ ID NO: 26, the amino acid sequence derived from SEQ ID NO: 26 by substitution, deletion or addition of one or more amino acids and functionally identical to SEQ ID NO: 26, and the amino acid sequence having at least 85% sequence identity to SEQ ID NO: 26, and comprises LCDR1, LCDR2 and LCDR3 set forth in SEQ ID NOs: 18, 19 and 20.

In some specific embodiments, the present disclosure provides an anti-CD47 antibody or antigen-binding fragment thereof, wherein the amino acid sequence of the heavy chain variable region is selected from the group consisting of SEQ ID NO: 27, the amino acid sequence derived from SEQ ID NO: 27 by substitution, deletion or addition of one or more amino acids and functionally identical to SEQ ID NO: 27, and the amino acid sequence having at least 85% sequence identity to SEQ ID NO: 27, and comprises HCDR1, HCDR2, and HCDR3 set forth in SEQ ID NOs: 1, 2 and 11; and the amino acid sequence of the light chain variable region is selected from the group consisting of SEQ ID NO: 24, the amino acid sequence derived from SEQ ID NO: 24 by substitution, deletion or addition of one or more amino acids and functionally identical to SEQ ID NO: 24, and the amino acid sequence having at least 85% sequence identity to SEQ ID NO: 24, and comprises LCDR1, LCDR2 and LCDR3 set forth in SEQ ID NOs: 12, 13 and 14.

In some specific embodiments, the present disclosure provides an anti-CD47 antibody or antigen-binding fragment thereof, wherein the amino acid sequence of the heavy chain variable region is selected from the group consisting of SEQ ID NO: 23, the amino acid sequence derived from SEQ ID NO: 23 by substitution, deletion or addition of one or more amino acids and functionally identical to SEQ ID NO: 23, and the amino acid sequence having at least 85% sequence identity to SEQ ID NO: 23, and comprises HCDR1, HCDR2, and HCDR3 set forth in SEQ ID NOs: 7, 8 and 9; and the amino acid sequence of the light chain variable region is selected from the group consisting of SEQ ID NO: 28, the amino acid sequence derived from SEQ ID NO: 28 by substitution, deletion or addition of one or more amino acids and functionally identical to SEQ ID NO: 28, and the amino acid sequence having at least 85% sequence identity to SEQ ID NO: 28, and comprises LCDR1, LCDR2 and LCDR3 set forth in SEQ ID NOs: 18, 19 and 20.

In some specific embodiments, the anti-CD47 antibody according to the present disclosure is a murine-derived antibody, which further comprises a heavy chain constant region of murine-derived IgG1, IgG2, IgG3, IgG4, or variants thereof, and a light chain constant region of murine-derived kappa chain or variants thereof.

In some preferred embodiments, the anti-CD47 murine-derived antibody according to the present disclosure further comprises a heavy chain constant region of murine-derived IgG1, IgG2, or variants thereof, and a light chain constant region of murine-derived kappa chain or variants thereof.

In some specific embodiments, the present disclosure provides an anti-CD47 humanized antibody or antigen-binding fragment thereof, wherein (1) the amino acid sequence of the heavy chain variable region is selected from:

(c1) amino acid sequences as set forth in SEQ ID NO: 29, SEQ ID NO: 30, and SEQ ID NO: 31, (c2) amino acid sequences derived from the amino acid sequences set forth in (c1) by substitution, deletion or addition of one or more amino acids and functionally identical or similar to the amino acid sequences as set forth in (c1), and (c3) amino acid sequences having at least 80% sequence identity to the amino acid sequences set forth in (c1); and (2) the amino acid sequence of the light chain variable region is selected from:

(c4) amino acid sequences as set forth in SEQ ID NO: 32, SEQ ID NO: 33, and SEQ ID NO: 34, (c5) amino acid sequences derived from the amino acid sequences set forth in (c4) by substitution, deletion or addition of one or more amino acids and functionally identical or similar to the amino acid sequences as set forth in (c4), and (c6) amino acid sequences having at least 80% sequence identity to the amino acid sequences set forth in (c4).

In some specific embodiments, the present disclosure provides an anti-CD47 humanized antibody or antigen-binding fragment thereof, wherein the amino acid sequence of the heavy chain variable region is selected from the group consisting of SEQ ID NO: 29, the amino acid sequence derived from SEQ ID NO: 29 by substitution, deletion or addition of one or more amino acids and functionally identical to SEQ ID NO: 29, and the amino acid sequence having at least 85% sequence identity to SEQ ID NO: 29; and the amino acid sequence of the light chain variable region is selected from the group consisting of SEQ ID NO: 32, the amino acid sequence derived from SEQ ID NO: 32 by substitution, deletion or addition of one or more amino acids and functionally identical to SEQ ID NO: 32, and the amino acid sequence having at least 85% sequence identity to SEQ ID NO: 32.

In some specific embodiments, the present disclosure provides an anti-CD47 humanized antibody or antigen-binding fragment thereof, wherein the amino acid sequence of the heavy chain variable region is selected from the group consisting of SEQ ID NO: 30, the amino acid sequence derived from SEQ ID NO: 30 by substitution, deletion or addition of one or more amino acids and functionally identical to SEQ ID NO: 30, and the amino acid sequence having at least 85% sequence identity to SEQ ID NO: 30; and the amino acid sequence of the light chain variable region is selected from the group consisting of SEQ ID NO: 33, the amino acid sequence derived from SEQ ID NO: 33 by substitution, deletion or addition of one or more amino acids and functionally identical to SEQ ID NO: 33, and the amino acid sequence having at least 85% sequence identity to SEQ ID NO: 33.

In some specific embodiments, the present disclosure provides an anti-CD47 humanized antibody or antigen-binding fragment thereof, wherein the amino acid sequence of the heavy chain variable region is selected from the group consisting of SEQ ID NO: 31, the amino acid sequence derived from SEQ ID NO: 31 by substitution, deletion or addition of one or more amino acids and functionally identical to SEQ ID NO: 31, or the amino acid sequence having at least 85% sequence identity to SEQ ID NO: 31; and the amino acid sequence of the light chain variable region is selected from the group consisting of SEQ ID NO: 34, the amino acid sequence derived from SEQ ID NO: 34 by substitution, deletion or addition of one or more amino acids and functionally identical to SEQ ID NO: 34, and the amino acid sequence having at least 85% sequence identity to SEQ ID NO: 34.

In some specific embodiments, the present disclosure provides an anti-CD47 humanized antibody or antigen-binding fragment thereof, wherein the amino acid sequence of the heavy chain variable region is selected from the group consisting of SEQ ID NO: 29, the amino acid sequence derived from SEQ ID NO: 29 by substitution, deletion or addition of one or more amino acids and functionally identical to SEQ ID NO: 29, and the amino acid sequence having at least 85% sequence identity to SEQ ID NO: 29, and comprises HCDR1, HCDR2, and HCDR3 set forth in SEQ ID NOs: 10, 2 and 11; and the amino acid sequence of the light chain variable region is selected from the group consisting of SEQ ID NO: 32, the amino acid sequence derived from SEQ ID NO: 32 by substitution, deletion or addition of one or more amino acids and functionally identical to SEQ ID NO: 32, and the amino acid sequence having at least 85% sequence identity to SEQ ID NO: 32, and comprises LCDR1, LCDR2 and LCDR3 set forth in SEQ ID NOs: 12, 13 and 14.

In some specific embodiments, the present disclosure provides an anti-CD47 humanized antibody or antigen-binding fragment thereof, wherein the amino acid sequence of the heavy chain variable region is selected from the group consisting of SEQ ID NO: 30, the amino acid sequence derived from SEQ ID NO: 30 by substitution, deletion or addition of one or more amino acids and functionally identical to SEQ ID NO: 30, and the amino acid sequence having at least 85% sequence identity to SEQ ID NO: 30, and comprises HCDR1, HCDR2, and HCDR3 set forth in SEQ ID NOs: 4, 5 and 6; and the amino acid sequence of the light chain variable region is selected from the group consisting of SEQ ID NO: 33, the amino acid sequence derived from SEQ ID NO: 33 by substitution, deletion or addition of one or more amino acids and functionally identical to SEQ ID NO: 33, and the amino acid sequence having at least 85% sequence identity to SEQ ID NO: 33, and comprises LCDR1, LCDR2 and LCDR3 set forth in SEQ ID NOs: 15, 16 and 17.

In some specific embodiments, the present disclosure provides an anti-CD47 humanized antibody or antigen-binding fragment thereof, wherein the amino acid sequence of the heavy chain variable region is selected from the group consisting of SEQ ID NO: 31, the amino acid sequence derived from SEQ ID NO: 31 by substitution, deletion or addition of one or more amino acids and functionally identical to SEQ ID NO: 31, and the amino acid sequence having at least 85% sequence identity to SEQ ID NO: 31, and comprises HCDR1, HCDR2, and HCDR3 set forth in SEQ ID NOs: 7, 8 and 9; and the amino acid sequence of the light chain variable region is selected from the group consisting of SEQ ID NO: 34, the amino acid sequence derived from SEQ ID NO: 34 by substitution, deletion or addition of one or more amino acids and functionally identical to SEQ ID NO: 34, and the amino acid sequence having at least 85% sequence identity to SEQ ID NO: 34, and comprises LCDR1, LCDR2 and LCDR3 set forth in SEQ ID NOs: 18, 19 and 20.

In some embodiments, the present disclosure provides an anti-CD47 humanized antibody or antigen-binding fragment thereof, wherein the heavy chain comprises a heavy chain constant region of humanized IgG1, IgG2, IgG3, IgG4 or variants thereof, and the light chain comprises a light chain constant region of humanized kappa, lambda chain, or variants thereof.

In a preferred embodiment of the present disclosure, the murine-derived anti-CD47 antibody or antigen-binding fragment thereof may further comprise a light chain constant region of murine-derived kappa, lambda chain, or variants thereof, and/or further comprise a heavy chain constant region of murine-derived IgG1, IgG2, IgG3, IgG4, or variants thereof.

In a preferred embodiment of the present disclosure, the antibody light chain of the anti-CD47 chimeric antibody or antigen-binding fragment thereof further comprises a light chain constant region of murine-derived kappa, lambda chain, or mutant sequences thereof. The antibody heavy chain of the anti-CD47 chimeric antibody or antigen-binding fragment thereof further comprises a heavy chain constant region of murine-derived IgG1, IgG2, IgG3, IgG4, or mutant sequences thereof, and preferably comprises a heavy chain constant region of humanized IgG1 or IgG2, or IgG4 constant region that significantly reduces ADCC (antibody-dependent cell-mediated cytotoxicity) after amino acid mutation.

In some specific embodiments, the anti-CD47 humanized antibody or antigen-binding fragment thereof of the present disclosure further comprises a heavy chain constant region of humanized IgG1, IgG2, IgG3, IgG4, or variants thereof, and a light chain constant region of humanized kappa chain, lambda chain, or variants thereof. In some preferred embodiments, the anti-CD47 humanized antibody or antigen-binding fragment thereof of the present disclosure further comprises a heavy chain constant region of humanized IgG1, IgG2, or variants thereof, and a light chain constant region of humanized kappa chain or variants thereof.

In some embodiments, the present disclosure provides an anti-CD47 antibody or antigen-binding fragment thereof, wherein the antigen-binding fragment is Fab, Fv, sFv or F(ab)2.

Another aspect of the present disclosure provides an isolated nucleic acid encoding the anti-CD47 antibody or antigen-binding fragment thereof according to the present disclosure.

In some specific embodiments, the isolated nucleic acid according to the present disclosure, wherein the nucleotide sequence encoding the amino acid sequence of the heavy chain variable region is set forth in SEQ ID NO: 35, SEQ ID NO: 36 or SEQ ID NO: 37; and the nucleotide sequence encoding the amino acid sequence of the light chain variable region is set forth in SEQ ID NO: 38, SEQ ID NO: 39 or SEQ ID NO: 40.

In a specific embodiment, the isolated nucleic acid according to the present disclosure, wherein the nucleotide sequence encoding the heavy chain variable region SEQ ID NO: 29 is set forth in SEQ ID NO: 35; the nucleotide sequence encoding the light chain variable region SEQ ID NO: 32 is set forth in SEQ ID NO: 38.

In a specific embodiment, the isolated nucleic acid according to the present disclosure, wherein the nucleotide sequence encoding the heavy chain variable region SEQ ID NO: 30 is set forth in SEQ ID NO: 36; the nucleotide sequence encoding the light chain variable region SEQ ID NO: 33 is set forth in SEQ ID NO: 39.

In a specific embodiment, the isolated nucleic acid according to the present disclosure, wherein the nucleotide sequence encoding the heavy chain variable region SEQ ID NO: 31 is set forth in SEQ ID NO: 37; the nucleotide sequence encoding the light chain variable region SEQ ID NO: 34 is set forth in SEQ ID NO: 40.

Another aspect of the present disclosure provides an expression vector expressing the anti-CD47 antibody or antigen-binding fragment thereof of the present disclosure. The expression vector according to the present disclosure comprises the isolated nucleic acid molecule of the present disclosure.

Another aspect of the present disclosure provides a host cell transformed with the expression vector as described above.

In some embodiments, the host cell according to the present disclosure is selected from prokaryotic cells and eukaryotic cells. In some embodiments, the host cell is bacteria, preferably *Escherichia coli*. In another preferred embodiment, the host cell is mammalian cells.

Another aspect of the present disclosure provides a method for producing the anti-CD47 antibody or antigen-binding fragment thereof of the present disclosure, comprising expressing the antibody in the host cell and isolating the antibody from the host cell.

Another aspect of the present disclosure provides a pharmaceutical composition comprising the anti-CD47 humanized antibody or antigen-binding fragment thereof of the present disclosure and a pharmaceutically acceptable carrier. In some embodiments, the present disclosure provides a pharmaceutical composition comprising the anti-CD47 humanized antibody or antigen-binding fragment thereof of the present disclosure, and also other active components, such as other antibodies, targeting drugs, and the like. In some embodiments, the pharmaceutically acceptable carrier is selected from the group consisting of antioxidants, polypeptides, proteins, hydrophilic polymers, amino acids, saccharides, chelating agents, alditols, ions, and surfactants. In a specific embodiment, the pharmaceutically acceptable carrier is a buffered aqueous solution. In another specific embodiment, the pharmaceutically acceptable carrier is in the form of liposomes.

The anti-CD47 humanized antibody or antigen-binding fragment thereof of the present disclosure can be combined with a pharmaceutically acceptable carrier, diluent or excipient to prepare a pharmaceutical preparation suitable for oral or parenteral administration. The routes of administration include, but are not limited to oral, intradermal, intramuscular, intraperitoneal, intravenous, intracerebral, intraocular, intratracheal, subcutaneous, and intranasal routes. The preparation can be administered by any means, for example, by infusion or bolus injection, by the means of absorption through epithelium or skin mucosa (for example, oral mucosa or rectum, etc.). Administration can be systemic or local. The preparation can be prepared by methods known in the art, and contains a carrier, diluent or excipient conventionally used in the field of pharmaceutical preparations.

Another aspect of the present disclosure provides a method for inhibiting CD47 activity, comprising administering the anti-CD47 antibody or antigen-binding fragment thereof of the present disclosure or the pharmaceutical composition of the present disclosure to a subject in need thereof.

Another aspect of the present disclosure provides use of the anti-CD47 antibody or antigen-binding fragment thereof of the present disclosure or the pharmaceutical composition of the present disclosure in the manufacture of a medicament for inhibiting CD47 activity. In some embodiments, the medicament for inhibiting CD47 activity is used to treat leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma. In some embodiments, the present disclosure provides use of the above-mentioned anti-CD47 antibody or antigen-binding fragment thereof or the pharmaceutical composition of the present disclosure in the manufacture of anti-tumor drugs. Preferably, the tumor is selected from the group consisting of leukemia, lymphoma, breast cancer, lung cancer, gastric cancer, intestinal cancer, esophageal cancer, ovarian cancer, kidney cancer, bladder cancer, pancreatic cancer, glioma and melanoma.

The anti-CD47 antibody or antigen-binding fragment thereof provided by the present disclosure has a significant anti-tumor effect, can significantly inhibit tumor growth, and does not have significant hemagglutination activity. The humanized antibody, whose immunogenicity is greatly reduced, effectively eliminates the rejection of exogenous monoclonal antibodies by human immune system and can be used in the manufacture of medicaments for the treatment of various tumor diseases with broad market prospects.

Definitions

Unless otherwise defined, the meanings of scientific and technical terms used herein are those commonly understood by those skilled in the art. The nomenclature and techniques used in cell and tissue culture, molecular biology, as well as protein and oligo/polynucleotide chemistry and hybridization described herein are well known and commonly used in the art. Standard techniques are used for recombinant DNA, oligonucleotide synthesis, tissue culture and transformation (e.g. electroporation, lipofection). The enzymatic reaction and purification techniques are carried out according to the manufacturer's instructions or methods commonly used in the art or described herein. The aforementioned techniques and methods are generally used according to what's well known in the art and what's described in the multiple comprehensive and more specific documents cited and discussed in this specification. Reference could be made to, Sambrook et al., Molecular Cloning: A Laboratory Manual (2nd edition, Cold Spring Harbor Laboratory Press, Cold Spring Harbor, New York (1989)). The nomenclature as well as laboratory methods and techniques used in analytical chemistry, synthetic organic chemistry, and medical and pharmaceutical chemistry described herein are well known and commonly used in the art.

In the present disclosure, the term "at least 80% sequence identity" refers to at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity. In the present disclosure, the term "at least 85% sequence identity" refers to at least 85%, 86%, 87%, 88%, 89%, 90%, 91%, 92%, 93%, 94%, 95%, 96%, 97%, 98%, 99%, or 100% sequence identity. In some preferred embodiments, the sequence identity described in the present disclosure may be at least 90%, 91%, 92%, 93%, 94%, 95%, 96%, 97%, 98%, 99%, or 100%. Sequence comparison and determination of percent identity between two sequences can be performed by the BLASTN/BLASTP algorithm on the website of National Center For Biotechnology Institute.

In an antibody molecule, three hypervariable regions of the light chain and three hypervariable regions of the heavy chain are arranged relative to each other in a three-dimensional space to form an antigen-binding surface. The antigen-binding surface is complementary to the three-dimensional surface of the bound antigen, and the three hypervariable regions of each heavy chain and light chain are referred as "complementarity determining region" or "CDR". The assignment of amino acids to each domain is defined by Kabat "Sequences of Proteins of Immunological Interest" (National Institutes of Health, Bethesda, Maryland (1987 and 1991)) or Chothia and Lesk (J. Mol. Biol. 196:901-917 (1987), Chothia et al., Nature 342:878-883 (1989)).

The "antigen-binding fragment" of the present disclosure refers to following fragment with antigen-binding activity: Fab fragment, Fab' fragment, F(ab')2 fragment, and Fv fragment and scFv fragment that bind to human CD47. The Fv fragment comprises a heavy chain variable region and a light chain variable region of the antibody but no constant region, and it is the smallest antibody fragment with all antigen binding sites. Generally, Fv antibody also comprises a polypeptide linker between the VH and VL domains, and is able to form the structure required for antigen binding. Different linkers may also be utilized to link the two variable regions of antibody to form a polypeptide chain, which is called single-chain antibody or single-chain Fv (scFv).

The antibody of the present disclosure refers to an immunoglobulin molecule or an immunologically active part thereof, that is, a molecule that contains antigen-binding sites that specifically bind to the antigen (through immunological reaction). "Specific binding" means that an antibody reacts with one or more antigenic determinants of an antigen but does not react with other polypeptides, or it binds to other polypeptides with very low affinity ($Kd>10^{-6}$). Antibodies include but are not limited to polyclonal, monoclonal, chimeric, dAb (domain antibody), single chain, Fab, Fab' and F(ab')2 fragment, Fv, scFv and Fab expression library. A monoclonal antibody (mAb) is the antibody obtained from a single cloned cell line, and the said cell line is not limited to eukaryotic, prokaryotic or phage cloned cell lines. A monoclonal antibody or antigen-binding fragment thereof can be obtained by recombination using, for example, hybridoma technology, recombination technology, phage display technology, and synthesis technology such as CDR grafting, or other existing technology.

The "murine-derived antibody" of the present disclosure is a monoclonal antibody against human CD47 produced according to the knowledge and skills in the art. During the production, the test subject is injected with the CD47 antigen, and then the hybridomas expressing the antibody with the desired sequence or functional property are isolated.

The "chimeric antibody" of the present disclosure is an antibody formed by fusing the variable regions of a murine-derived antibody with the constant regions of a human antibody, which can reduce the immune response induced by the murine-derived antibody. To establish a chimeric antibody, it is necessary to establish a hybridoma secreting murine-derived specific monoclonal antibodies first, clone the variable region genes from the mouse hybridoma cells, and then clone the constant region genes of the human antibody as needed, and chimeric genes formed by linking the mouse variable region with the human constant region genes are inserted into a human vector. Finally, the chimeric antibody is expressed in a eukaryotic system or a prokaryotic system.

The "humanized antibody" of the present disclosure is also called a CDR grafted antibody, which is the antibody produced by grafting mouse CDR sequences into the variable region framework (FR) of a human antibody. Such variable region framework sequences can be obtained from public DNA databases or public references, for example, from the ImMunoGeneTics (IMGT) website http://imgt.cines.fr or from the Journal of Immunoglobulin, 2001ISBN012441351.

DETAILED DESCRIPTION

Figure 1:
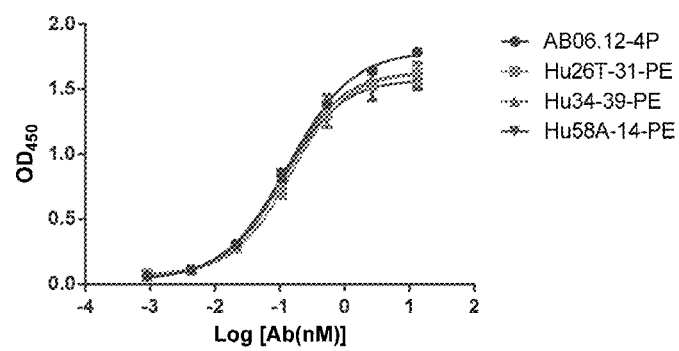
FIG. 1 shows the ELISA results of the binding activity test of anti-CD47 humanized antibodies against monkey CD47.

The following representative examples are used to illustrate the present disclosure better, rather than to limit the scope of protection of the present disclosure. The experimental methods without conditions indicated in the following examples are usually carried out according to conventional conditions, such as the antibody technology experiment manual and molecular cloning manual of Cold Spring Harbor, or according to the conditions recommended by the raw material or commodity manufacturers. The materials and reagents used in the examples are all commercially available unless otherwise specified.

Example 1 Preparation of Antigen Protein and Positive Control Antibody

1. Construction of Expression Vector of Antigen Protein and Positive Control Antibody (1) Construction of Expression Vector of Antigen Protein A gene fragment encoding the full length of CD47 protein was synthesized, and the amino acid sequence is shown in SEQ ID NO: 41. This fragment was cloned into the eukaryotic expression plasmid pTargeT to generate the CD47 expression plasmid pTargeT-CD47.

The amino acid sequence of the extracellular region of the human CD47 protein was fused with the amino acid sequence of hIgG1-Fc or his-tag, and the designed amino acid sequences are shown in SEQ ID NO: 42 and SEQ ID NO: 43, respectively. After codon optimization of the above amino acid sequences, the tagged CD47 protein extracellular region coding fragments, CD47-hFc and CD47-his, were synthesized and cloned into the eukaryotic expression plasmid pHR respectively to generate the respective expression plasmid pHR-CD47-hFc and pHR-CD47-his.

The amino acid sequence of the extracellular region of the human CD47 protein was fused with the amino acid sequence of mIgG1-Fc, and the designed amino acid sequence is shown in SEQ ID NO: 44. After codon optimization of the amino acid sequence, a complete expression plasmid pcDNA3.1(+)-TPA-CD47-mIgG1-Fc was constructed.

The sequence of SIRPα is shown in SEQ ID NO: 45. After codon optimization of the amino acid sequence, a complete expression plasmid pcDNA3.1(+)-SIRPα-myc-His was constructed.

(2) Construction of Expression Vector of Positive Control Antibody

The antibody AB6.12-IgG4P (abbreviated as AB06.12-4P herein) disclosed in the patent application WO2013/119714 was used as a positive control antibody. The amino acid sequences of AB06.12-4P are as follows:

heavy chain amino acid sequence of AB06.12-4P is shown in SEQ ID NO: 46; and light chain amino acid sequence of AB06.12-4P is shown in SEQ ID NO: 47.

The amino acid sequence corresponding to the above antibody sequences were artificially optimized to obtain the heavy chain and light chain expression plasmids pcDNA3.1(+)-SHC025-hG4 and pcDNA3.1(+)-SHC025-hk of the positive control antibody AB06.12-4P. The heavy chain gene fragment was cloned into the eukaryotic expression plasmid pHR containing the light chain constant region of IgG4 to obtain the heavy chain eukaryotic expression plasmid pHR-SHC025-hG4-4PE and the light chain expression plasmid pcDNA3.1(+)-SHC025-hk of AB06.12-4P.

2. Expression and Purification of Antigen Protein and Positive Control Antibody (1) Construction of Stable Transgenic Cell Line of Antigen Protein CHO-K1 cells (Shanghai Institute of Biochemistry and Cell Biology, Chinese Academy of Sciences) were electrotransfected with eukaryotic expression plasmid pTargeT-CD47 under a square pulse of 15 msec at a voltage of 160V and then cultured in an incubator at 37° C. and 5% CO2. After 24 h, the cells were subjected to selection with culture medium containing 500 μg/ml G418. After 16 days, the positive rate of pool was detected by FACS. The cells transfected with plasmid were plated ($1 \times 10^6$ cells/ml of cell density, 100 μl/well), and incubated with PE mouse anti-human CD47 antibody (BD, 556046). Flow cytometer (BD, FACSJazz) was used to read the mean value at a wavelength of 585 nm, and data analysis was performed using GraphPad. The positive cell lines were subcloned, and a CHO-K1 cell line was selected, which expressed CD47 at a high level and was named CHO-K1-E5.

(2) Expression of Tagged Antigen Protein and Positive Control Antibody 293F cells were inoculated into a 1 L cell culture flask with a density of $0.5 \times 10^6$ cells/ml. Fresh and pre-warmed FreeStyle 293 expression medium was added to make the total volume of 250 mL. The cells were cultured in a humidified CO2 incubator at 37° C. and 8% CO2 overnight. 500 μl of 1 mg/ml PEI solution was added to 8.5 mL FreeStyle 293 expression medium and mixed well. 250 μg of plasmid to be transfected was added to 8.5 ml FreeStyle 293 expression medium and mixed well, wherein, the tagged antigen protein plasmids pHR-CD47-hFc, pHR-CD47-his, pcDNA3.1(+)-TPA-CD47-mIgG1-Fc and pcDNA3.1(+)-SIRPα-myc-His were transfected respectively, and the heavy chain plasmid pHR-SHC025-hG4-4PE and the light chain plasmid pcDNA3.1(+)-SHC025-hk of positive control antibody AB06.12-4P were co-transfected. The FreeStyle 293 expression medium containing PEI was added to the expression medium containing plasmid and mixed well, then the mixture was added to the cells, and cultured in a humidified CO2 incubator at 37° C. and 8% CO2. The cells were fed on the 1st and 3rd day after cell transfection with 2.5 ml of 200 mM glutamine and 5 ml of 180 g/L glucose per flask. The cell culture supernatant was collected when the cell viability dropped to 65%-75%. The cell culture was centrifuged at 1,500 rpm for 5 min to collect the supernatant, and then centrifuged at 8,000 rpm for 20 min to collect the supernatant.

(3) Affinity Chromatography Purification

Different affinity chromatography columns were used to perform purification by using AKTA machine (GE, AKTA pure-150) according to the properties of the proteins (see Table 1 for affinity chromatography columns suitable for different proteins). The specific purification steps are as follows.

TABLE 1

Affinity chromatography columns suitable for different proteins

| Protein | Column | Brand | Model |
|---|---|---|---|
| Murine monoclonal antibody (hybridoma)/ CD47-mFc | Protein G prepacked column | Bestchrom | Ezfast Protein G 4FF |
| CD47-his/ SIRPα-myc-His | NI prepacked column | GE | His Trap, HP 5 ml |
| CD47-hFc/ chimeric antibody, humanized antibody | Protein A prepacked column | GE | Hi Trap, Mabselect SuRe 5 ml |
|  | Protein A self-packed column | GE | Mabselect LX 18 ml |

Cleaning

The equipment and pipelines were cleaned with ultrapure water for 2 min with a flow rate of 10 mL/min, and then the chromatography system was cleaned with 0.1M NaOH.

Column Connection

The chromatography column was connected to the chromatography equipment and rinsed with ultrapure water for 5 min, and then the chromatography system was rinsed with 0.1M NaOH for 30 min with a retention time of 5 min.

Equilibration

Five CVs (column volume) of 20 mM PB+0.15M NaCl, pH 7.2 was used to equilibrate the column.

Sample Loading

The supernatant from cell expression was loaded to the column with a retention time of 5 min.

Post-Equilibration

Five CVs 20 mM PB+0.15M NaCl, pH 7.2 was used to equilibrate.

Elution

Elution was performed with 50 mM acetic acid (pH=3.4), for a retention time of 5 min. Collection started when UV280 reached about 50 mAu, and stopped when UV280 dropped to about 50 mAu. The sample was adjusted to the pH of 7.0 with 1M Tris-HCl (pH 9.0).

Re-Equilibration

Three CVs of 20 mM PB+0.15M NaCl, pH 7.2, was used to equilibrate with a retention time of 5 min.

On-Column Cleaning

Cleaning was performed with 0.1M NaOH for 30 min with a retention time of 5 min.

Cleaning and Preservation

Cleaning was performed with purified water for 10 minutes, and then 2 CVs of 20% ethanol.

Example 2 Preparation of Monoclonal Antibodies

1. Preparation of Hybridomas (1) Animal Immunization

The experimental SJL mice were immunized with different tagged CD47 proteins together with adjuvant. 50 μg of antigen was used for the first shoot, and subsequently 25 μg of antigen was used for immunization.

The immune adjuvants used in the experiments may be QuickAntibody-Mouse5W (Beijing Biodragon immunotech. Co., Ltd.), TiterMax (Sigma), CpG (GenScript Biotechnology Co., Ltd.), or Alum (thermo) adjuvant. Different tagged CD47 protein samples were added dropwise to the adjuvant solution with vortex to mix thoroughly. The dosages of the adjuvant were referred to the instructions. After the mixture was mixed well and formed a water-in-oil emulsion, the SJL mice were immunized.

Cell lines that express high level of CD47, such as CCRF-CEM and CHO-K1-E5, were also used to immunize mice to produce antibodies. The cultured human acute lymphoblastic leukemia cells (CCRF-CEM) and CHO-K1-E5 positive cells obtained in Example 1 were treated with trypsin and then centrifuged at 1,000 rpm for 5 min. The supernatant was discarded and the cell pellets were resuspended in PBS. Part of the sample was taken out to perform cell counting, and the remaining sample was centrifuged at 1,000 rpm for 5 min. The supernatant was discarded and the cell pellet was resuspended in PBS. An appropriate amount of PBS was added to obtain a cell suspension of $1\times10^8$ cells/ml. Each mouse in the experimental group was immunized with $1\times10^7$ cells.

The immunization protocol is shown in Table 2.

TABLE 2

Mouse Immunization Protocol

| Group | Antigen | Adjuvant | Immunization Route* |
|---|---|---|---|
| 1 | PBS | None |  |
| 2 | CD47-his/ CD47-mFc | Quick Antibody-Mouse5W | i.m. |
| 3 | CD47-his/ CD47-mFc | Titer Max/CpG/Alum | s.c./i.m. |
| 4 | CD47-mFc | Quick Antibody-Mouse5W | i.m. |
| 5 | CD47-mFc | Titer Max/CpG/Alum | s.c./i.m. |
| 6 | CCRF-CEM/ CHO-K1-E5 | None | i.p. |

*i.m.: intramuscular injection; s.c.: subcutaneous injection; i.p.: intraperitoneal injection.

(2) Hybridoma Fusion

Acquisition and preparation of spleen cells. The mice after booster immunization were sacrificed and soaked in 75% alcohol. The spleen was dissected out, ground with a grinding rod, and filtered through a cell strainer to prepare a single cell suspension. The spleen cell suspension was centrifuged at 2,000 rpm for 5 min, and the supernatant was discarded. 2 mL red blood cell lysate was added to lyse red blood cells at room temperature for 2 min and PBS was added to reach 20 mL. After centrifugation at 1,500 rpm for 7 min, the supernatant was discarded. Viable cells were counted after resuspension. The Sp2/0 cells in the culture flask were collected and after centrifuged at 1,000 rpm for 5 min, the supernatant was discarded. Viable cells were counted after resuspension. The spleen cells were mixed with Sp2/0 cells at a ratio of 1:1 and subjected to centrifugation at 1,500 rpm for 7 min, the supernatant was discarded. The cells were resuspended in 20 mL electroporation buffer. After centrifugation at 1,500 rpm for 7 min, the supernatant was discarded and the step was repeated once. The cells were resuspended with an appropriate amount of electroporation buffer to ensure the cell concentration of about $2\times10^7$ cells/mL. The cell suspension was added to a 9 mL electroporation tank for fusion. After fusion, the cell suspension was transferred to 15 mL RPMI 1640 complete medium containing 20% FBS and then left at room temperature for 20 min. The fused cells were resuspended with RPMI 1640 medium containing 1×HAT, 1×BIOMYC3, and 20% FBS. The cell suspension was added to several 96-well cell culture plates at 100 µl/well to ensure that the cell volume per well was about 4×10⁴ cells/well, and the plates was placed in a 37° C. cell incubator. After 5 days, additional 100 µL of RPMI 1640 complete medium containing 20% FBS, 1×HAT, and 1×BIOMYC-3 was added to each well.

(3) Screening of Hybridoma and Subcloning

After one week of fusion, the supernatants of culture were collected and used for screening the hybridoma supernatants that can bind to CD47-his protein or CD47 on cell surface by ELISA. CD47-his was used to screen for antibodies against CD47 instead of hFc and mFc. The ability of the hybridoma supernatant to block the CD47-SIRPα interaction was analyzed by ELISA. SIRPα-myc-his was coated on ELISA plates. The mixture of recombinant humanized CD47-hFc and hybridoma supernatant was added and incubated for 2 h. HRP-labeled anti-human IgG Fc specific antibody (Jackson Immuno Research) was added and incubated for 1 h. Microplate reader was used to detect absorbance at 450 nm. The hybridoma parent clones showing binding and blocking activities in the screening experiments were expanded. The binding and blocking activities were retested, and the hybridoma positive clones with binding and blocking activities were obtained by screening again.

The positive cell lines were subcloned by the limiting dilution method. After one week of culture, the binding activity to CD47 and the activity of blocking the CD47-SIRPα interaction of the supernatants were detected by ELISA. Three cell lines that showed positive results in the above two tests were obtained, respectively named as SHC025-26, SHC025-34 and SHC025-58.

2. Identification of Antibody Subtypes

The antibody subtypes were identified according to the instructions of the mouse antibody subtype identification kit "SBA Clonotyping Systerm-057BL/6-HRP" (SouthernBiotech, Cat. No. 5300-05B). The results are shown in Table 3.

TABLE 3

Identification results of antibody subtypes

| Antibody | Antibody subtype |
|---|---|
| SHC025-26 | IgG1/k |
| SHC025-34 | IgG2c/k |
| SHC025-58 | IgG2b/k |

3. Preparation of Monoclonal Antibodies

According to the activity analysis results of the supernatants from cell culture, the parent clones of monoclonal antibodies SHC025-26, SHC025-34, and SHC025-58 were identified and expanded. The culture medium was 1640 medium containing 10% fetal bovine serum, 1×NAEE, 1× sodium pyruvate, and 1% penicillin-streptomycin double antibiotics. When the cell confluence was >80%, the cells were subcultured and expanded. 50 ml of the supernatant was collected and the antibody was purified. The obtained antibody was subjected to SDS-PAGE gel electrophoresis and showed a good purity.

4. Sequencing of Monoclonal Antibodies

The subcloned positive hybridomas were expanded, and an appropriate amount of cells was used for total RNA extraction according to the instructions of RNeasy Plus Mini Kit (Qiagen, 74134). The first strand of cDNA was synthesized using Prime Script 1st strand cDNA Synthesis Kit (Takara, 6110A).

Specific primers were designed according to the variable region of the mouse antibody subtype, and 5' end of the primers contained the homologous arm sequence for homologous recombination with the eukaryotic expression vector. PCR amplification for the variable region of antibodies was performed using cDNA as a template to obtain the gene fragments of the light chain variable region and heavy chain variable region of the mouse antibody respectively. The design of primers refers to references: 1. Anke Krebber, Susanne Bornhauser, Jorg Burmester etal. Reliable cloning of functional antibody variable domains from hybridomas and spleen cell repertoires employing a reengineered phage display system. Journal of Immunological Methods, 1997, 201: 35-55; 2. Simon KorenMiha KosmačAnja Colja Venturini etal. Antibody variable-region sequencing as a method for hybridoma cell-line authentication, 2008, 78: 1071-1078. DNA sequencing was performed and the results are shown in Table 4.

TABLE 4

Sequence table of anti-CD47 murine-derived monoclonal antibody

| Antibody | Amino acid sequence of the heavy chain variable region | Amino acid sequence of the light chain variable region |
|---|---|---|
| SHC025-26 | SEQ ID NO: 21 | SEQ ID NO: 24 |
| SHC025-34 | SEQ ID NO: 22 | SEQ ID NO: 25 |
| SHC025-58 | SEQ ID NO: 23 | SEQ ID NO: 26 |

Example 4 Construction of Chimeric Antibodies

The purified DNA fragments of the light chain and the heavy chain variable regions of the mouse antibody (see Example 1 for the purification steps) were respectively co-transformed into *Escherichia coli* DH5α competent cells with the linearized eukaryotic expression plasmid containing the light chain constant region or the heavy chain constant region of the human antibody. The mixture was spread evenly on the surface of the agar plates containing the corresponding antibiotics. The agar plates were incubated in a 37° C. constant temperature incubator overnight, and then several single colonies were picked out for DNA sequencing. The chimeric antibodies with correct sequences were named SHC025-26CHI, SHC025-34CHI, and SHC025-58CHI.

The positive clones with correct sequences were inoculated in 2×YT liquid medium containing the corresponding antibiotics and cultured at 37° C. for more than 12 hours with shaking. The bacterial cells were collected for plasmid extraction to obtain the plasmids expressing the light chain and the heavy chain of the chimeric antibody. The concentration and purity of the plasmids were detected by a nucleic acid quantitative analyzer.

The plasmids for chimeric antibodies were transfected into HEK293E cells, and the antibodies were expressed and purified. The purity, activity and affinity were tested and analyzed.

By sequencing, it was found that there was one cysteine in the heavy chain CDR position 118 of SHC025-26 and one cysteine in the light chain CDR position 56 of SHC025-58. During the antibody expression, the cysteine in CDR region would randomly pair with the other cysteines on the antibody molecule to form a disulfide bridge, which thereby would greatly affect the purity of the antibody. To solve this problem, the amino acid sequences of SHC025-26CHI and SHC025-58CHI were modified as follows: C118 of SHC025-26CHI heavy chain was mutated to T and the obtained antibody was named SHC025-26CHI-T; C56 of SHC025-58CHI light chain was mutated to A and the obtained antibody was named SHC025-58CHI-A. The mutant sequences were constructed by site-directed mutagenesis. The results of the chimeric antibody sequencing are shown in Table 5.

TABLE 5

Sequences of anti-CD47 chimeric antibodies

| Chimeric antibody | Amino acid sequence of the heavy chain variable region | Amino acid sequence of the light chain variable region |
|---|---|---|
| SHC025-26CHI | SEQ ID NO: 21 | SEQ ID NO: 24 |
| SHC025-26CHI-T | SEQ ID NO: 27 | SEQ ID NO: 24 |
| SHC025-34CHI | SEQ ID NO: 22 | SEQ ID NO: 25 |
| SHC025-58CHI | SEQ ID NO: 23 | SEQ ID NO: 26 |
| SHC025-58CHI-A | SEQ ID NO: 23 | SEQ ID NO: 28 |

Example 5 Construction and Production of Humanized Antibodies

Based on the results of activity analysis and affinity KD value of chimeric antibodies, SHC025-34CHI, SHC025-58CHI-A, and SHC025-26CHI-T were modified to humanized antibodies.

To construct the humanized antibodies, the variable regions of SHC025-34CHI, SHC025-58CHI-A, and SHC025-26CHI-T antibody were compared with the mouse antibody sequences in the ImMunoGeneTics (IMGT) to determine their murine-derived germlines. After homology comparison, it was found that the FR region sequences of the heavy chain variable region of SHC025-34CHI, SHC025-58CHI-A, and SHC025-26CHI-T antibody were the most similar to the germline gene of the mouse antibody IGHV1-8*01, IGHV3-21*04, and IGHV1-2*02 respectively; the FR sequences of the light chain variable region of the antibodies were the most similar to the mouse antibody IGKV3-11*01, IGKV1-5*01 and IGKV4-1*01 respectively. With the framework region sequence FR1-FR3 of SHC025-34CHI/SHC025-58CHI-A antibody as templates, full human framework regions with similar 3D structure but low immunogenicity were screened in the human framework region library to replace FR1-FR3 sequence of SHC025-34CHI/SHC025-58CHI-A. The full-length sequences of the heavy/light chain were 3D modeled and compared structurally with the heavy/light chain sequences of the original antibodies. Considering the antigenicity and 3D structural similarity, 6 humanized heavy chain variable regions (see SEQ ID NOs: 48, 49, 50, 51, 52, and 53) and 4 humanized light chain variable regions (see SEQ ID NOs: 54, 55, 56, and 57) of SHC025-34CHI, and 6 humanized heavy chain variable regions (see SEQ ID NOs: 58, 59, 60, 61, 62, and 63) and 5 humanized light chain variable regions (see SEQ ID NOs: 64, 65, 66, 67, and 68) of SHC025-58CHI-A were ultimately selected for further optimization. More than 95% of non-CDR regions of SHC025-34CHI or SHC025-58CHI-A antibody were humanized. The variable region sequences of the heavy and light chain of SHC025-26CHI-T were used to perform structural alignment analysis in Protein Data Bank. The FR1-FR3 sequences with the highest similarity were selected to replace the murine-derived sequences, and the amino acid sites that displayed key role in structure stabilization of the antibody in the structural simulation were mutated back to murine-derived amino acid residues. Finally, 4 humanized heavy chain variable regions (see SEQ ID NOs: 69, 70, 71, and 72) and 2 humanized light chain variable regions (see SEQ ID NOs: 73 and 74) of SHC025-26CHI-T were obtained.

The amino acid sequences of the light chain and heavy chain variable region of humanized antibody obtained above were reversely transcribed into their corresponding nucleotide sequences, and oligonucleotide fragments containing complementary sequences between adjacent fragments were generated. The oligonucleotide fragments were annealed and assembled by Overlap PCR. Then nucleotide fragments of the entire light chain and heavy chain variable regions were amplified using specific primers (5' end contained the homologous arm sequence for homologous recombination with the eukaryotic expression vector). The purified nucleotide fragments of the light chain variable region were co-transformed into Escherichia coli DH5α competent cells with the linearized eukaryotic expression plasmid containing light chain constant region of IgG4. The purified nucleotide fragments of the heavy chain variable region were co-transformed into Escherichia coli DH5α competent cells with the eukaryotic expression plasmid containing heavy chain constant region of IgG4 containing S228P/L235E mutation. The competent cells with the transformed plasmid were spread evenly on the surface of the agar plates containing the corresponding antibiotics. The agar plates were incubated in a 37° C. constant temperature incubator overnight, and then several single colonies were picked out for DNA sequencing.

The positive clones with correct sequences were inoculated in 2×YT liquid medium containing the corresponding antibiotics and cultured at 37° C. with shaking for more than 12 hours. The bacterial cells were collected for plasmid extraction to obtain the expression plasmids for the light chain and the heavy chain of humanized antibodies. The concentration and purity of the plasmids were detected by a nucleic acid quantitative analyzer.

The plasmids were transfected into HEK293E cells, and a large number of antibodies were expressed and purified. The purity, activity and affinity were tested and analyzed.

The humanized antibodies with good purity, activity and affinity were selected, and named as Hu26T-31-PE, Hu34-39-PE, and Hu58A-14-PE. The sequences are shown in Table 6. The sources of humanized antibodies are shown in Table 7.

TABLE 6

Sequence table of anti-CD47 humanized antibodies

| | Amino acid sequence | | Nucleotide sequence | |
|---|---|---|---|---|
| Humanized antibody | Heavy chain variable region | Light chain variable region | Heavy chain variable region | Light chain variable region |
| Hu26T-31-PE | SEQ ID NO: 29 | SEQ ID NO: 32 | SEQ ID NO: 35 | SEQ ID NO: 38 |
| Hu34-39-PE | SEQ ID NO: 30 | SEQ ID NO: 33 | SEQ ID NO: 36 | SEQ ID NO: 39 |
| Hu58A-14-PE | SEQ ID NO: 31 | SEQ ID NO: 34 | SEQ ID NO: 37 | SEQ ID NO: 40 |

TABLE 7

Information of humanized sequences

| Source of humanized sequence | Recombinant humanized sequence |
|---|---|
| heavy chain | |
| X62106 Homsap IGHV1-2*02 F | SEQ ID NO: 29 |
| X92343 Homsap IGHV1-46*01 F | SEQ ID NO: 30 |
| HM855688 Homsap IGHV3-21*04 F | SEQ ID NO: 31 |
| light chain | |
| X97473 Homsap IGLV3-9*01 F | SEQ ID NO: 32 |
| X71966 Homsap IGLV3-21*01 F | SEQ ID NO: 33 |
| Z73648 Homsap IGLV4-69*01 F | SEQ ID NO: 34 |

Example 6 Antibody Binding Activity to Monkey CD47 (by ELISA)

The binding activity of antibodies was analyzed by protein based ELISA. Cynomolgus CD47-His (0.1 μg/well, ACRO Biosystems, Cat. No. CD7-052H1-50 μg) was coated on 96-well ELISA plates. The anti-CD47 antibodies of the present disclosure was used as the primary antibody and added to the ELISA plates in 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5 h. AB06.12-4P was used as the positive control antibody and Anti-Human IgG HRP (Jackson, 109-035-003, 1:10000) was used as the secondary antibody. Color developing solution TMB (3,3',5,5'-tetramethylbenzidine) was added to the plate, and microplate reader (Thermo, Multiskan FC) was used to read OD450 value after termination of the reaction. $EC_{50}$ was generated by GraphPad. The result is shown in FIG. 1.

The experimental results show that humanized anti-CD47 antibodies Hu26T-31-PE, Hu34-39-PE and Hu58A-14-PE of the present disclosure can bind to cynomolgus CD47, and the binding ability is equivalent to that of the positive control antibody AB06.12-4P.

Example 7 Antibody Binding Activity to Human CD47 (by ELISA)

Figure 2:
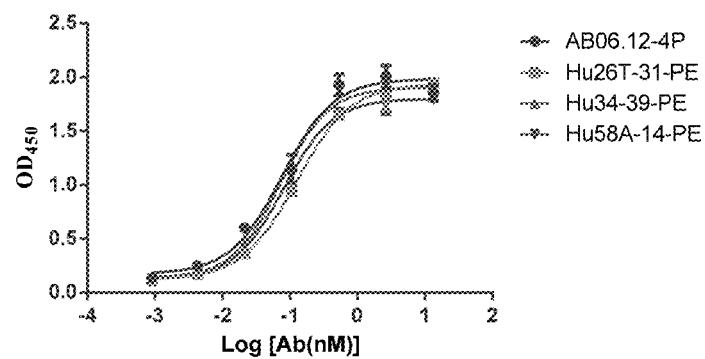
FIG. 2 shows the ELISA results of the binding activity test of anti-CD47 humanized antibodies against human CD47.

The binding activity of antibodies was analyzed by ELISA. Human CD47-His protein (0.1 μg/well, prepared in Examples 1 and 2) was coated on 96-well ELISA plates, and the ELISA plates were incubated at 37° C. for 2 h. After washing 3 times with 1×PBST, the ELISA plates were blocked with 5% non-fat milk at 4° C. overnight. The plates were washed 3 times with 1×PBST. The anti-CD47 antibodies of the present disclosure were used as the primary antibody and added to the ELISA plates at 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5 h. The plates were washed 3 times with 1×PBST. AB06.12-4P was used as the positive control antibody and Anti-Human IgG HRP (Jackson, 109-035-003, 1:10000) was used as the secondary antibody. Then the plates were incubated at 37° C. for 40 min. Color developing solution TMB was added after the plates were washed 5 times with 1×PBST, and microplate reader (Thermo, Multiskan FC) was used to read OD450 value after termination of the reaction. $EC_{50}$ was generated by GraphPad. The result is shown in FIG. 2.

The experimental results show that humanized anti-CD47 antibodies Hu26T-31-PE, Hu34-39-PE and Hu58A-14-PE of the present disclosure can bind to human CD47, and the binding ability is equivalent to that of the positive control antibody AB06.12-4P.

Example 8 Antibody Binding to Cell Surface CD47 (by ELISA)

Figure 3:
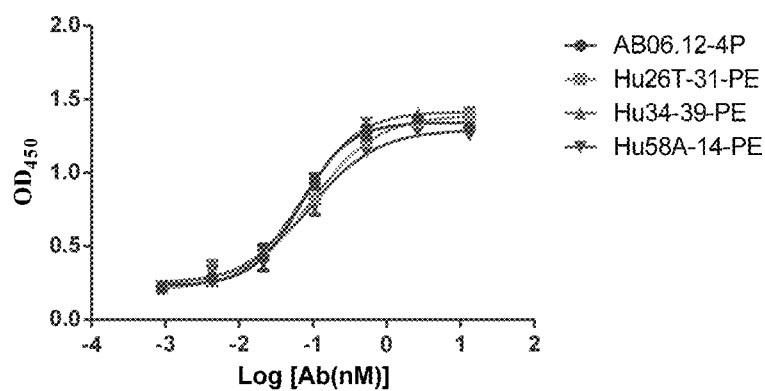
FIG. 3 shows the ELISA results of the binding activity test of anti-CD47 humanized antibodies against CD47 on cell surface.

The binding activity of antibodies was analyzed by cell based ELISA. CHO-K1-E5 cells were plated at $1 \times 10^5$ cells per well and cultured overnight at 37° C. and 5% CO2. On the second day, the cells were fixed with 4% paraformaldehyde, then blocked with non-fat milk for 1 h, and later washed gently with 1×PBS. The anti-CD47 antibody of the present disclosure was used as the primary antibody and added to the plates in 5-fold gradient dilution with a total of 8 concentrations: 2000 ng/mL, 400 ng/mL, 80 ng/mL, 16 ng/mL, 3.2 ng/mL, 0.64 ng/mL, 0.128 ng/mL, and 0 ng/mL respectively. The plates were incubated at 37° C. for 1.5 h. AB06.12-4P was used as the positive control antibody and Anti-Human IgG HRP (Jackson, 109-035-003, 1:10,000) was used as the secondary antibody. Color developing solution TMB was added, and microplate reader (Thermo, Multiskan FC) was used to read OD450 value after termination. $EC_{50}$ was generated by GraphPad. The result is shown in FIG. 3.

The experimental results show that humanized anti-CD47 antibodies Hu26T-31-PE, Hu34-39-PE and Hu58A-14-PE of the present disclosure can bind to CD47 on cell surface, and the binding ability is equivalent to that of the positive control antibody AB06.12-4P.

Example 9 Affinity Assay of Antibody to Human CD47 Protein

The affinity of the humanized anti-CD47 antibodies prepared in Examples 1 and 2 to the antigen CD47(19-136)-hFC was determined by Fortebio Octet. First, the antigen CD47(19-136)-hFc was labeled with biotin, and then put into 10 kD cut-off ultrafiltration tube with PBS for desalting by centrifugation. This step was repeated 3-4 times. The actual concentration of the biotin-labeled antigen (CD47-hFc-Biotin) was determined by Nanodrop machine. CD47-hFc-Biotin was diluted with SD buffer (0.02% Tween20+ 0.1% BSA solution) to a concentration of 5 μg/ml. The humanized anti-CD47 antibody was diluted with SD buffer in 4-fold gradient dilution to make the concentrations of 10 μg/ml, 2.5 m/ml, 0.625 m/ml and 0 μg/ml. SA sensor was used to solidify the antigen, and affinity assay was performed according to the manual of fortebio Octet RED96. The specific parameters and experimental results are shown in Table 8.

TABLE 8

Affinity assay of antibody to human CD47 protein

| Antibody | KD (M) | kon(1/Ms) | kdis(1/s) |
|---|---|---|---|
| Hu26T-31-PE | 5.87E−11** | 1.04E+06 | 6.13E−05 |
| Hu34-39-PE | 1.13E−10 | 6.69E+06 | 7.58E−04 |
| Hu58A-14-PE | 9.46E−11 | 1.78E+06 | 1.68E−04 |
| AB06.12-4P | 1.01E−10 | 4.80E+06 | 4.85E−04 |

The experimental results show that Hu26T-31-PE has significantly higher affinity for binding to human CD47 protein than the positive control antibody.

Figure 4:
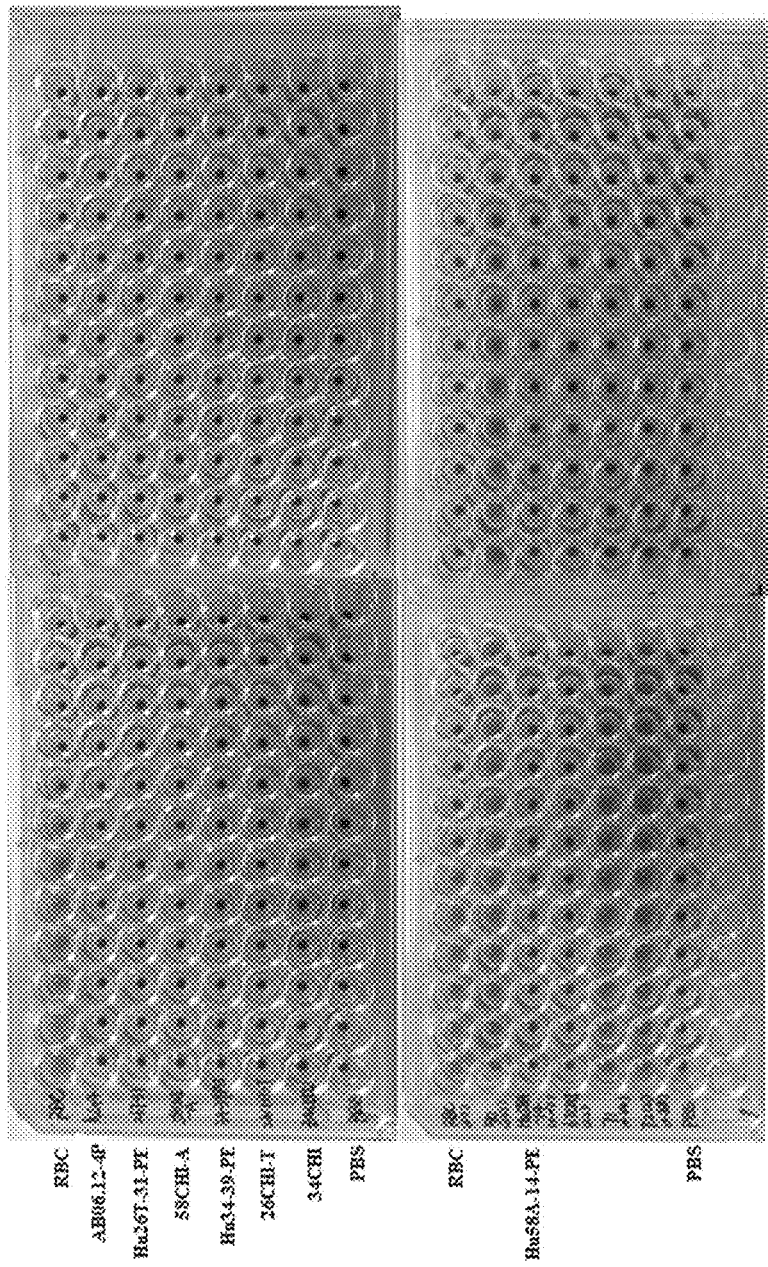
FIG. 4 shows the result of erythrocyte agglutination, RBC (red blood cell) as positive control and PBS as blank control.

Example 10 Hemagglutination Assay 5 mL blood sample was added to 40 mL PBS. The mixture was centrifuged at 2000 rpm for 5 min and the supernatant was discarded. The cell pellet was washed three times with PBS and then resuspended in PBS. According to the hematocrit, a 2% red blood cell suspension was prepared. The initial concentration of the antibody to be analyzed was 1-20 µM at a 2-fold dilution, a total of 24 concentration gradients. In round-bottom 96-well plates, 50 µL of the above-mentioned antibodies of different concentrations was added, and then 50 ul of the 2% red blood cell suspension was added. The mixture was mixed well, placed at room temperature and monitored for agglutination after 2 h. Rabbit polyclonal RBC antibody (Rockland, 109-4139) was used as a positive control for hemagglutination and the results are shown in FIG. 4. As shown in FIG. 4, the concentration of the antibodies (rabbit polyclonal RBC antibody, AB06.12-4P antibody and the test antibodies of the present disclosure) from left to right in the 96-well plates was diluted in a 2-fold gradient starting from 20 uM. RBC indicated the positive control group, in which rabbit polyclonal RBC antibody caused significant hemagglutination), and PBS indicated the blank control group. If there is no cell agglutination, the red blood cells will fall to the bottom of the well as a small dot with smooth edge. Dot with slightly vague edge indicates agglutination of a small amount of red blood cells. If the red blood cells form flaky shape and cover the whole bottom of the well, this indicates agglutination of most of the red blood cells.

It has been reported that the anti-CD47 antibody Hu5F9-G4 disclosed in the patent application WO2011/143624 can cause significant agglutination of red blood cells within the same concentration range, which is a common undesirable property of anti-CD47 antibodies. However, under the same conditions, Hu26T-31-PE, Hu34-39-PE, and Hu58A-14-PE of the present disclosure did not cause hemagglutination as shown in the experimental results, indicating that the antibodies of the present disclosure are significantly superior to the Hu5F9-G4 antibody in this respect.

Example 11 Detection of CD47 Blocking Activity by FACS

The ability of the anti-CD47 antibody provided by the present disclosure to block SIRPa from binding to CD47 on cell surface was detected by FACS.

Figure 5:
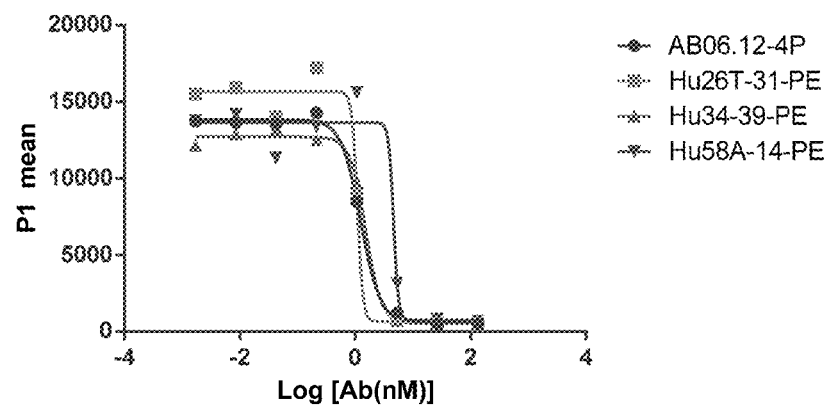
FIG. 5 shows the result of blocking activity of anti-CD47 humanized antibodies by FACS detection.

CHO-K1-E5 cells positive for CD47 were used as a CD47 provider. In the presence of a serially diluted anti-CD47 antibody, the binding of CD47 to SIRPa was monitored. PE Streptavidin (Biolegend, 405203, 1:200) was used as the secondary antibody to monitor the changes of SIRPa-Biotin, and AB06.12-4P was used as a positive control which blocked SIRPa from binding to CD47 on cell surface. Flow cytometer (BD, FACSJazz) was used to read the mean value at a wavelength of 585 nm and $IC_{50}$ was generated by GraphPad. The result is shown in FIG. 5.

The experimental results show that the blocking activity ranking from high to low is: Hu26T-31-PE≥Hu34-39-PE≥AB06.12-P>Hu58A-14-PE.

Example 12 Anti-Tumor Test in Human Gastric Cancer NUGC-4 Transplanted Tumor Model 1. Experimental Materials
(1) Experimental Cells and Animals
NUGC-4 human gastric cancer cells were purchased from American Type Culture Collection (ATCC).
NOD-Scid mice, female, 5-8 weeks old, weighing 18-20 grams, were purchased from Shanghai Lingchang Biotechnology Co., Ltd.
(2) Test Samples and Controls
The reference antibody isotype IgG4 (Cat. No. AB170091) was purchased from Crown Bioscience Co., Ltd. and used as a negative control.
Before the test, the humanized anti-CD47 antibody of the present disclosure was prepared at two concentrations of 0.6 mg/mL and 0.3 mg/mL in PBS, and Isotype IgG4 and AB 06.12-4P were prepared at 0.6 mg/mL.
(3) Experimental Methods
NUGC-4 human gastric cancer cells were cultured with RMPI1640 medium containing 10% fetal bovine serum, 100 U/mL penicillin and 100 µg/mL streptomycin in a 37° C., 5% CO2 incubator. The cells were digested, treated with 2 mL 1×EDTA solution and passaged once a week. When the cell confluence reached 80%-90%, the cells were collected, counted, and seeded. PBS containing $5\times10^6$ cells was mixed with 100 uL Matrigel (final volume of 200 µL). The mouse was injected with the mixture on the right back side, $5\times10^6$ cells/mouse. The mice were grouped when the tumor grew to a volume of 150-200 mm$^3$ and administered intraperitoneally with the test sample three times per week. The tumor diameter was measured with a vernier caliper three times per week and the tumor volume was calculated by a calculation equation of V=0.5a×b$^2$, where a and b represent the long and short diameters of the tumor, respectively. The anti-tumor efficacy of antibodies was evaluated by the relative tumor growth rate T/C (%). The calculation equation of the relative tumor growth rate T/C (%) is as follows: T/C %=TRTV/CRTV×100% (TRTV: treatment group RTV; CRTV: negative control group RTV). RTV=V21/V0, where V0 is the tumor volume measured at the time of being grouped and administered (Day 0), and V21 is the tumor volume measured at the 21th day of administration (Day 21). The tumor volumes on the last day (Day 21) of the administration group and the vehicle group were analyzed by t-test using GraphPad Prism. The results are shown in Table 9.

TABLE 9

Anti-tumor test results in human gastric cancer NUGC-4 transplanted tumor model

| Antibody | Dose (mg/kg) | T/C (%) | p (vs. Isotype IgG4) |
|---|---|---|---|
| Isotype IgG4 | 6 | 86.61 | — |
| AB06.12-4P | 6 | 18.82 | ** |
| Hu26T-31-PE | 3 | 12.24 | *** |
| Hu26T-31-PE | 6 | 2.96 | *** |
| Hu34-39-PE | 3 | 15.29 | *** |
| Hu34-39-PE | 6 | 3.45 | *** |

Comparing with Isotype IgG4, * indicates p < 0.001;  indicates p < 0.005.

Figure 6:
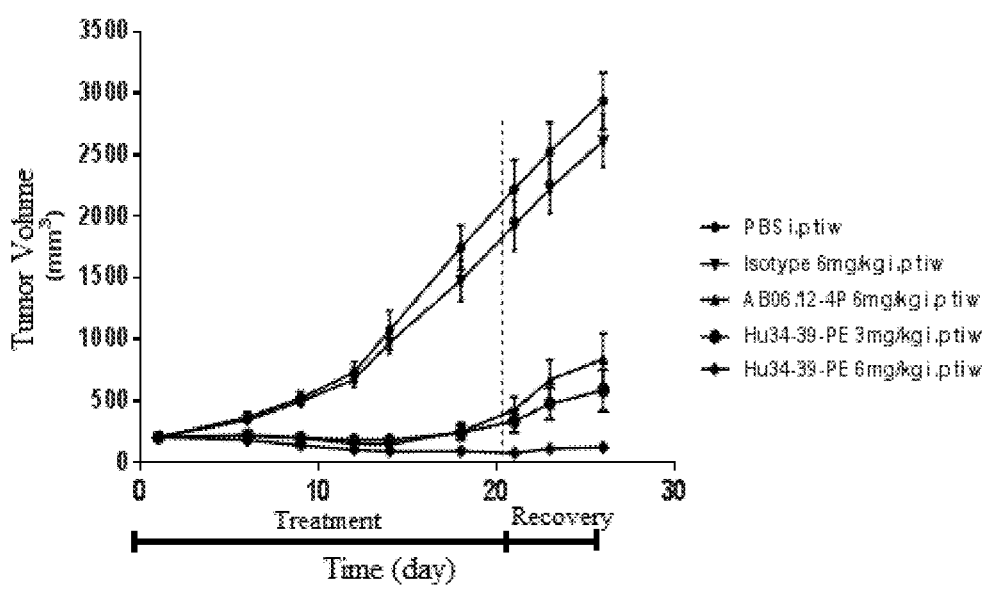
FIG. 6 shows the anti-tumor test result of anti-CD47 humanized antibody Hu34-39-PE in human gastric cancer NUGC-4 transplanted tumor model.
Figure 7:
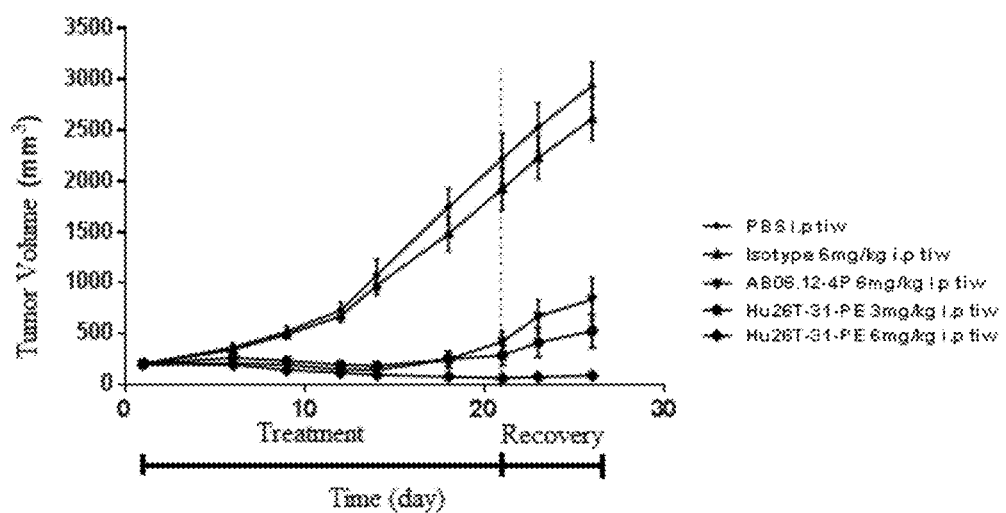
FIG. 7 shows the anti-tumor test result of anti-CD47 humanized antibody Hu26T-31-PE in human gastric cancer NUGC-4 transplanted tumor model.

Experimental results show that the antibodies of the present disclosure have a significant anti-tumor effect in NOD-SCID mice transplanted tumor model inoculated with human gastric cancer NUGC-4 cells. Hu26T-31-PE and Hu34-39-PE at a dose of 3 mg/kg show equivalent tumor-suppressive effect as the reference antibody AB06.12-4P at a dose of 6 mg/kg, while Hu26T-31-PE and Hu34-39-PE at a dose of 6 mg/kg show a better tumor-suppressive effect than the reference antibody AB06.12-4P at a dose of 6 mg/kg. One week after drug withdrawal, tumor recurrence occurred in the group of reference antibody at a dose of 6 mg/kg, while no recurrence occurred in the group of Hu26T-31-PE or Hu34-39-PE (FIG. 6 and FIG. 7). It indicates that the anti-CD47 antibodies of the present disclosure have unexpectedly better effect on inhibiting tumor growth.

The above examples demonstrate that the anti-CD47 antibodies of the present disclosure have a significant anti-tumor effect and can significantly inhibit tumor growth, suggesting that the antibody can be used in the manufacture of anti-tumor drugs and has a good market prospect.

Although the present disclosure has been described above in detail, those skilled in the art should understand that various modifications and changes can be made to the present disclosure without departing from the spirit and scope of the present disclosure. The scope of the present disclosure should not be limited to the detailed description above, but should be attributable to the appended claims.

The invention claimed is:

1. An anti-CD47 antibody or antigen-binding fragment thereof, comprising a heavy chain variable region and a light chain variable region, wherein
the heavy chain variable region comprises HCDR1, HCDR2 and HCDR3, and the amino acid sequences of HCDR1, HCDR2 and HCDR3 are set forth in SEQ ID NOs: 4, 5 and 6, respectively, and
the light chain variable region comprises LCDR1, LCDR2 and LCDR3, and the amino acid sequences of LCDR1, LCDR2 and LCDR3 are set forth in SEQ ID NOs: 15, 16 and 17, respectively.

2. The anti-CD47 antibody or antigen-binding fragment thereof according to claim 1, wherein the antibody is a murine monoclonal antibody, a human-murine chimeric antibody, or a humanized antibody.

3. The CD47 antibody or antigen-binding fragment thereof according to claim 1, wherein the antibody further comprises a heavy chain constant region of murine IgG1, IgG2, or variants thereof, and a light chain constant region of murine kappa chain or variants thereof.

4. The anti-CD47 antibody or antigen-binding fragment thereof according to claim 1, wherein
the amino acid sequence of the heavy chain variable region is SEQ ID NO: 22, and the amino acid sequence of the light chain variable region is SEQ ID NO: 25.

5. The anti-CD47 antibody or antigen-binding fragment thereof according to claim 1, wherein
the amino acid sequence of the heavy chain variable region is SEQ ID NO: 30, and the amino acid sequence of the light chain variable region is SEQ ID NO: 33.

6. An isolated nucleic acid encoding the anti-CD47 antibody or antigen-binding fragment thereof according to claim 1.

7. The nucleic acid according to claim 6, wherein
(1) the nucleotide sequence encoding the amino acid sequence of the heavy chain variable region is set forth in SEQ ID NO: 36 and
(2) the nucleotide sequence encoding the amino acid sequence of the light chain variable region is set forth in SEQ ID NO: 39.

8. A method of treating a disease comprising administering the anti-CD47 antibody or antibody-binding fragment thereof according to claim 1 to a subject in need thereof, wherein the disease is leukemia, lymphoma, breast cancer, lung cancer, gastric cancer, intestinal cancer, esophageal cancer, ovarian cancer, cervical cancer, kidney cancer, bladder cancer, pancreatic cancer, glioma and/or melanoma.

* * * * *